US011484500B2

(12) United States Patent
De Beer

(10) Patent No.: US 11,484,500 B2
(45) Date of Patent: *Nov. 1, 2022

(54) HYBRIDOSOMES, COMPOSITIONS COMPRISING THE SAME, PROCESSES FOR THEIR PRODUCTION AND USES THEREOF

(71) Applicant: ANJARIUM BIOSCIENCES AG, Zollikon (CH)

(72) Inventor: Joel De Beer, Zollikon (CH)

(73) Assignee: ANJARIUM BIOSCIENCES AG, Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/732,567

(22) Filed: Jan. 2, 2020

(65) Prior Publication Data
US 2020/0222324 A1    Jul. 16, 2020

Related U.S. Application Data

(62) Division of application No. 15/112,180, filed as application No. PCT/IB2015/050436 on Jan. 20, 2015, now Pat. No. 10,561,610.

(60) Provisional application No. 61/929,559, filed on Jan. 21, 2014.

(51) Int. Cl.
| | |
|---|---|
| A61K 9/127 | (2006.01) |
| C12N 15/88 | (2006.01) |
| A61K 47/69 | (2017.01) |
| C07K 16/28 | (2006.01) |
| C12N 15/113 | (2010.01) |

(52) U.S. Cl.
CPC .......... *A61K 9/1272* (2013.01); *A61K 9/1271* (2013.01); *A61K 9/1277* (2013.01); *A61K 47/6911* (2017.08); *A61K 47/6913* (2017.08); *C07K 16/2896* (2013.01); *C12N 15/113* (2013.01); *C12N 15/88* (2013.01); *C07K 2317/54* (2013.01); *C07K 2317/55* (2013.01); *C12N 2310/14* (2013.01); *C12N 2310/531* (2013.01); *Y02A 50/30* (2018.01)

(58) Field of Classification Search
CPC .. A61K 9/1271; A61K 9/1272; A61K 9/1277; A61K 47/6913; A61K 47/6911; C12N 15/88; C12N 15/113; C12N 2310/531; C12N 2310/14; C07K 2317/54; C07K 16/2896; C07K 2317/55; Y02A 50/423
See application file for complete search history.

(56) References Cited

U.S. PATENT DOCUMENTS

| | | |
|---|---|---|
| 5,552,155 A | 9/1996 | Bailey et al. |
| 10,561,610 B2 | 2/2020 | De Beer |
| 2011/0251156 A1 | 10/2011 | Shen et al. |
| 2013/0053426 A1 | 2/2013 | Seow et al. |
| 2013/0195765 A1 | 8/2013 | Gho et al. |
| 2014/0308304 A1 | 10/2014 | Manoharan et al. |
| 2016/0354313 A1 | 12/2016 | De Beer |

FOREIGN PATENT DOCUMENTS

| | | |
|---|---|---|
| JP | 2013-128452 | 7/2013 |
| WO | WO 2004/002453 | 1/2004 |
| WO | WO 2008/092153 | 7/2008 |
| WO | WO 2010/119256 | 10/2010 |
| WO | WO 2011/097480 | 8/2011 |
| WO | WO 2013/048734 | 4/2013 |
| WO | WO 2015/110957 | 7/2015 |

OTHER PUBLICATIONS

Alberts et al., 1983, Molecular Biology of the Cell, Garland Publishing, NY, Chapter 17:965.
Bailey et al., 1994, "Modulation of membrane fusion by asymmetric transbilayer distributions of amino lipids", Biochemistiy, 33:12573-12580.
Banerjee et al., 2012, "Poly(styrene-co-maleic Acid)-Based pH-sensitive Liposomes Mediate Cytosolic Delivery of Drugs for Enhanced Cancer Chemotherapy", International J of Pharmaceutics, 436:786-797.
Banik et al., 2017, "pH induced interaction of DPPC with a fluorescent dye in langmuir and langmuir blodgett (LB) films", Molecular Crystals and Liquid Crystals, 643(1):255-265.
De La Pena et al., 2009, "Artificial exosomes as tools for basic and clinical immunology", J of Immunological Methods, NL, 344(2):121-132.
Jayaraman et al., 2012, "Maximizing the potency of siRNA lipid nanoparticles for hepatic gene silencing in vivo", Angewandte Chemie, International Edition, 57:8529-8533.
Lo Meins et al., 2013, "Hybrid polymer/lipid vesicles: state of the art and future perspectives", Materials Today, 16(10):397-402.
Nanjundappa et al., 2012, "Novel CD8+ T cell-based vaccine stimulates Gp120-specific CTL responses leading to therapeutic and long-term immunity in transgenic HLA-A2 mice", Vaccine, 30(24):3519-3525.
Palmerini et al., 2006, "Role of cholesterol, DOTAP, and DPPC in prostasome/spermatozoa interaction and fusion", J of Membrane Biology, 211(3):185-190.
Semple et al., 2010, "Rational design of cationic lipids for siRNA delivery", Nature Biotechnology, 28(2):172-178.
Yuyama et al., 2012, "Sphingolipid-modulated Exosome Secretion Promotes Clearance of Amyloid-β by Microglia", J of Biological Chemistry, 287(14):10977-10989.
International Search Report and Written Opinion dated Oct. 19, 2015 for PCT/IB2015/050436 (34 pages).

(Continued)

*Primary Examiner* — Robert S Cabral
(74) *Attorney, Agent, or Firm* — Jones Day

(57) ABSTRACT

The present invention provides a hybrid biocompatible carrier (hybridosome) which comprises structural and bioactive elements originating from at least one biocompatible delivery module (BDM) and at least one engineered drug encapsulation module (EDEM) comprising at least one tunable fusogenic moiety. The invention further provides pharmaceutical compositions comprising said hybridosomes, processes for their manufacture, as well as pharmaceutical uses and pharmaceutical methods based thereon.

39 Claims, 14 Drawing Sheets

(56) References Cited

OTHER PUBLICATIONS

Lu et al., "Influence of polymer size, liposomal composition, surface charge, and temperature on the permeability of pH-sensitive liposomes containing lipid-anchored poly (2-ethylacrylic acid)." International Journal of Nanomedicine 7:4917-4926 (2012).

HYBRIDOSOMES, COMPOSITIONS COMPRISING THE SAME, PROCESSES FOR THEIR PRODUCTION AND USES THEREOF

CROSS-REFERENCE TO RELATED APPLICATIONS

This application is a continuation of U.S. patent application Ser. No. 15/112,180, now U.S. Pat. No. 10,561,610, which is a national stage of International Patent Application No. PCT/IB2015/050436, filed Jan. 20, 2015, which claims the benefit of priority of U.S. Provisional Patent Application No. 61/929,559, filed Jan. 21, 2014.

FIELD OF THE INVENTION

The present invention relates to the field of pharmaceutical biocompatible carriers and the targeted delivery of active agents for therapeutic, prophylaxis, imaging, and diagnostic applications. More specifically, the invention relates to a biocompatible hybrid carrier resulting from controlled unification of a naturally secreted biocompatible delivery module (BDM) and an engineered drug encapsulation module (EDEM).

BACKGROUND OF THE INVENTION

Contemporary drug therapy approaches are mainly based on the development of new therapeutic molecules as well as on the advancement of combined treatment schedules. However, clinical efficacy of these approaches is inherently limited by their physical-chemistry, pharmacokinetics and cross-reactivity attributes, inadvertently arising from a restricted concentration at the intended site of action and an extensive overall bio-distribution.

In an effort to address this challenge, the emerging command of nanotechnology is facilitating the delivery of drug molecules to non-healthy organs, tissues and/or cells. The most advanced nanotechnology inspired drug delivery platforms are focused on the entrapment of therapeutically active molecules in synthetic lipid-based carrier systems. Encapsulation facilitates the isolation of a drug from the in vivo environment, hereby overcoming a drug's non-ideal properties, including limited solubility, serum stability, circulation half-life and biodistribution.

The ideal synthetic nanocarrier which is composed of non-toxic constituents and is specifically internalized by target cells remains elusive to date. Therefore, these systems don't harness the full potential that nanotechnology can provide. Insights into how molecules are transmitted in nature may provide the blueprint for efficient and biocompatible drug delivery vehicles.

It is known that cells exchange information through the secretion of soluble factors or by direct interaction. Recent studies have come to the conclusions that cells also release membrane-derived vesicles that have an impact on both neighboring and distant cells (Marcus & Leonard, 2013). These extracellular vesicles are secreted by most cells, and are physiological constituents of most biological fluids (Vlassov, Magdaleno, Setterquist, & Conrad, 2012). Extracellular vesicles entail the subtypes apoptotic bodies, microvesicles, and exosomes (EL Andaloussi, Mäger, Breakefield, & Wood, 2013)

Although the research on how extracellular vesicles can act as mediators of intercellular communication is still in its early stages, exploring their inherit role in delivering bioactive cargo from "donor" cells to "recipient" cells is contributing valuable insights into the complexity of optimal drug delivery. Various studies have identified several conditions in which extracellular vesicles can function as therapeutic carriers. There is increasing evidence that these carriers possess distinct characteristics rendering them pharmaceutically superior to synthetic drug carriers. Of particular significance for this superiority is a collection of membrane proteins and distinct lipids integrated in the surface composition of extracellular vesicles.

Several obstacles exist that hinder exploiting or mimicking natures' carriers for efficient drug delivery systems. Most notably, transforming extracellular vesicles from message couriers to drug carriers requires the introduction of therapeutic or diagnostic molecules exogenous to the "donor" cell. The respective engineering methodologies proposed to date include the use of bioengineering procedures on "donor" cells (i.e. genetic modification, viral transfection, toxic cationic lipofection, etc.) as well as vigorous or damaging manipulation mechanisms applied to isolated vesicles (i.e. electroporation, conjugation chemistry, etc.). These methods ultimately raise safety as well as scalability concerns and hamper a translation into the clinic. Other important issues that still need to be addressed include control over structural integrity of the carrier, efficient encapsulation of active cargo and the incorporation of additional targeting moieties.

Ideally, intricate bio-mimetic functionalization approaches requiring numerous bioactive membrane components incorporated into a synthetic nanocarrier could be circumvented if intact extracellular vesicle membranes would be exploited. Conversely, in order to overcome the dire consequences of biotechnological protocols, strategies to introduce therapeutic as well as targeting components exogenous to the extracellular vesicles, should preferably be independent of cellular manipulation. Based on these premises, it may be beneficial to replace bioengineering techniques with nanotechnological strategies employed in modern nano-particular drug delivery systems.

In view of the shortcomings mentioned above, it is an object of the invention to provide a novel pharmaceutical carrier with highly defined attributes, lacking the drawbacks of prior art carriers while synergizing the advantages of ex-vivo generated synthetic nanocarriers and in vivo occurring extracellular vesicles.

It is another object of the invention is to provide a pharmaceutical composition comprising said novel pharmaceutical carrier.

It is a further object of the invention to provide uses and methods based on said novel pharmaceutical carrier or a pharmaceutical comprising it for the treatment, monitoring, prevention, staging and/or diagnosis of a disease or condition It is a further object of the invention to provide a process for manufacturing said novel pharmaceutical carrier in a controllable way involving stimuli-responsive modules.

It is a further object of the invention to provide a method for delivering one or more bioactive agents into a cell, more particularly a cell selected from a leukocyte, a glial cell and a stem cell.

It is a further object of the invention to provide a method to produce the above pharmaceutical carrier in a controllable way involving stimuli-responsive modules.

Further purposes and advantages of this invention will appear as the description proceeds.

SUMMARY OF THE INVENTION

The present invention provides a hybrid biocompatible carrier (hybridosome) which comprises structural and bioactive elements originating from at least one biocompatible delivery module (BDM) and at least one engineered drug encapsulation module (EDEM) comprising at least one tunable fusogenic moiety.

The invention further provides a pharmaceutical composition comprising a hybridosome as defined above and at least one pharmaceutically acceptable carrier, adjuvant or excipient.

The invention still further provides a process for manufacturing a hybrid biocompatible carrier (hybridosome) which comprises structural and bioactive elements originating from at least one biocompatible delivery module (BDM) and at least one engineered drug encapsulation module (EDEM) comprising at least one tunable fusogenic moiety, said process comprising:

(a) providing at least one EDEM having at least one fusogenic moiety or a composition comprising the same;

(b) providing at least one BDM or a composition comprising the same;

(c) contacting said at least one EDEM with said at least one BDM at a pH below 7.4 and at a temperature of between 0° C. and 60° C., thereby uniting said at least one EDEM with said at least one BDM and producing said hybridosome; and optionally (d) purifying said hybridosome from non-fused EDEMs and/or BDMs.

The invention still further provides a method for delivering one or more bioactive agents into a leukocyte, said method comprising contacting a composition comprising a hybridosome including said one or more bioactive agents with a composition comprising said leukocyte, wherein said hybridosome results from the fusion of at least one EDEM comprising at least one tuneable fusogenic moiety with at least one leukocyte-derived BDM.

The invention still further provides a method for delivering one or more bioactive agents into a glial cell, said method comprising contacting a composition comprising a hybridosome including said one or more bioactive agents with a composition comprising said glial cell, wherein said hybridosome results from the fusion of at least one EDEM comprising at least one tuneable fusogenic moiety with at least one glial cell-derived BDM.

The invention still further provides a method for delivering one or more bioactive agents into a cell during an ex-vivo expansion, said method comprising contacting a composition comprising a hybridosome including said one or more bioactive agents with a composition comprising said cell, wherein said hybridosome results from the fusion of at least one EDEM comprising at least one tuneable fusogenic moiety with at least one BDM derived from said cell.

BRIEF DESCRIPTION OF THE DRAWINGS

The above and other characteristics and advantages of the invention will be more readily apparent through the following examples, and with reference to the appended drawings, wherein.

DETAILED DESCRIPTION

Figure 1:
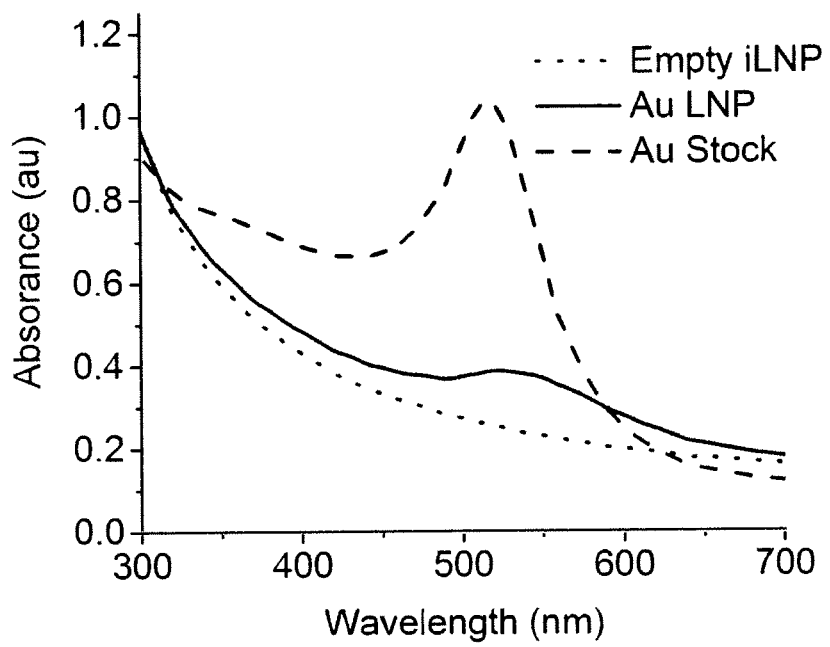
FIG. 1 is a graph showing the UV-Vis absorbtion spectra of Au-iLNPs, Au Stock and iLNPs.

In a first aspect the present invention provides a hybrid biocompatible carrier (hybridosome) which comprises structural and bioactive elements originating from at least one biocompatible delivery module (BDM) and at least one engineered drug encapsulation module (EDEM) comprising at least one tunable fusogenic moiety.

As used herein, the terms "hybrid biocompatible carrier" or "hybridosome" refer to a hybrid biocompatible carrier which comprises structural and bioactive elements (e.g., lipids, carbohydrates, fatty acids, polynucleotides or polypeptides) originating from at least one biocompatible delivery module (BDM) (e.g. exosomes, microvesicles, apoptotic bodies) and at least one engineered drug encapsulation module (EDEM) comprising a tunable fusogenic moiety. In a specific embodiment, the internal volume of the hybridosome contains at least one bioactive agents originating from a BDM secreted in vivo (e.g. endogenous polynucleotides, enzymes or polypeptides) and at least one bioactive agent encapsulated in an EDEM manufactured in vitro. In another embodiment, the internal volume of the hybridosome only comprises natural components originating from the BDMs and may be further treated. The hybridosome of the invention results from uniting one BDM with one EDEM, several BDMs with one EDEM, several EDEMs with one BDM, or several BDMs with several EDEMs. The uniting event may be controlled via the size of the BDMs and EDEMs, their respective charges, and the conditions applied during a uniting reaction such as the ratio BDM/EDEM, the pH, the temperature and the reaction time. Such a modular strategy to assemble a novel composition from separate units can offer a new level of engineering flexibility. This unification of messenger and therapeutic components could confer unique characteristics to the resulting hybrid carrier which are not otherwise attainable by the single systems.

As used herein, "Biocompatible Delivery Module (BDM)" refers to a naturally secreted vesicle comprising a lipid bilayer, which is produced in vivo and is released into the extracellular environment. BDMs are secreted by various types of cells, including but not limited to epithelial cells, tumor cells and other immune cells (e.g. mast cells, T and B lymphocytes, dendritic cells). BDMs used in the present invention are either isolated from physiological fluids or a tissue sample taken from a subject, preferably a human subject, or are isolated from culture mediums. In one specific embodiment, BDMs used in the present invention derive from a cell culture wherein the cells are either natural or have been previously immortalized and/or engineered. The cell culture may be homogeneous (one type of cells) or heterogeneous (several types of cells), and may be composed of isolated cells and/or tissue. BDMs can be isolated or derived from an organism including prokaryotes, eukaryotes, bacteria, fungi, yeast, invertebrates, vertebrates, reptiles, fish, insects, plants and animals. Media taken from cultured cells ("conditioned media", cell media, or cell culture media) may be a biological fluid.

BDMs may be collected and isolated using methods known to those of ordinary skill in the art. For instance, BDMs can be collected from a cell culture or a tissue supernatant by one or more techniques selected from the group consisting of, but not limited to, differential ultracentrifugation, gradient ultracentrifugation, filtration, tangential flow filtration (TFF), low-pressure track-etched membrane filtration and combinations thereof. In one embodiment, the BDMs used in the present invention are prepared by centrifugation of culture supernatant to pellet unwanted cell debris followed by ultracentrifugation to pellet exosomes, density gradient ultracentrifugation (for example, with sucrose gradient) or a combination of these methods.

BDMs useful for the present invention range in size from about 30 nm to about 2000 nm and may contain biologically active molecules (e.g. polynucleotide and/or polypeptides). Examples of BDMs include but are not limited to, "exosomes" (about 30 nm to about 200 nm in diameter), "microvesicles" (about 100 nm to about 2000 nm in diameter), and "apoptotic bodies" (about 300 nm to about 2000 nm in diameter). The term BDM is used interchangeably with "exosome", "microvesicle" or "apoptotic body", "membrane particles", "membrane vesicles", "exosome-like vesicles", "ectosome-like vesicles", "ectosomes" or "exovesicles". The BDM lipid bilayer is derived from membranes of the donor cell. BDMs derived from different cell types may show differences in lipid composition compared to the plasma membrane. During the genesis of exosomes, transmembrane and peripheral membrane proteins can be embedded in the vesicle membrane, and at the same time, cytosolic components may also be incorporated into the vesicles.

As used herein, the term "endogenous" refers to a compound naturally produced by a cell and derived from the cell. For example, a BDM contains an endogenous polypeptide if that polypeptide was produced within the cell the BDM is derived from.

As used herein the term "naturally secreted" as applied to a carrier, a particle, a vesicle or molecule refers to a carrier, a particle, a vesicle or molecule that is released to the environment from a cell, an organism or tissue by a process found in nature. For example, exosome that can be isolated from a source and which has not been physically translocated from within the boundaries of the source by a human in the laboratory is naturally secreted. A further non-limiting example for the process secreting particles in nature is the fusion of an intracellular organelle with the cell membrane or blebbing of the cell membrane.

As used herein, "Engineered Drug Encapsulation Module (EDEM)" refers to a vesicle comprising one or more membrane which has been produced in vitro. EDEMs useful in the present invention are selected from, but are not limited to, lipid-based nanoparticles (LNPs), liposomes, polymer-stabilized LNPs, cerasomes, sphingosomes, niosomes, polymersomes, synthetic-nanoparticle stabilized LNPs, core-shell lipid-polymer hybrid nanoparticles, natural membrane-derived LNPs, rapidly eliminated lipid nanoparticles (reLNPs) and natural membrane-coated LNPs. EDEMs used in the present invention have at least one structural property that enables their controlled uniting with BDMs. In one embodiment, said structural property is provided by one or more constituents of the lipid bilayer(s) of the EDEM. In one specific embodiment, the EDEM used in the present invention is an ionizable-LNP (iLNP).

EDEMs used in the present invention may have various morphologies. They may comprise either one lipid bilayer (unilamellar vesicle), a series of concentric bilayers separated by narrow aqueous compartments (multi-lamellar vesicle or MLV) or membrane forming polymers. Furthermore, conversely to BDMs, EDEMs are substantially homogeneous in size and density distribution. EDEMs used herein have a diameter (mean particle diameter) from about 15 to about 500 nm. In some embodiments, EDEMs have a diameter of about 300 nm or less, 250 nm or less, 200 nm or less, 150 nm or less, 100 nm or less, or 50 nm or less. In one specific embodiment, the EDEM used in the invention has a diameter from about 15 to about 150 nm.

EDEMs useful in the present invention are manufactured so as to display specific physicochemical characteristics. The physicochemical characteristics of each specific EDEMs may vary according to the nature and concentration of the active agent(s) entrapped therein, the membrane composition of the polymer membrane or lipid bilayer(s), the nature of the medium in which the EDEMs have been dispersed, their size and polydispersity. In one specific embodiment of the invention, the EDEMs comprise a lipid bilayer membrane including ionizable cationic lipids and helper lipids. In some specific embodiments, EDEMs used to generate the hybridosome of the invention are manufactured based on a molar ratio of DlinDMA:Chol:DSPC:PEG-Cer (40:40:17.5:2.5 molar ratio).

The manufacture of EDEMs can be carried out through a variety of ways known in the art, as disclosed for example in the following references. These include, for example, sonication, extrusion, high pressure/homogenization, microfluidization, detergent dialysis, calcium-induced fusion of small liposomes and lipid film hydration methods. For example, LNPs can be made using the previously described preformed vesicle method (Maurer et al., 2001). Typically, the method consists of extruding LNPs through a small-pore polycarbonate membrane to reduce LNPs sizes to a well-defined size distribution and in a later stage, if required, therapeutic agents are loaded into the preformed vesicles. Alternatively, EDEMS can be prepared via spontaneous self-assembly in a microfluidic system. Protocols for producing well-defined size distribution with such manufacturing techniques are known in the art (Belliveau et al., 2012). Preferably, the EDEMs used in the present invention are substantially homogeneous in size and density distribution to facilitate separation from subpopulations of BDMs and hybridosomes. The separation is made by using techniques well known in the art, for instance, size exclusion chromatography and density gradient centrifugation. In one specific embodiment, the density of the EDEMs is lower than the one of the hybridosome, thereby facilitating the separation of the hybrid vesicles from the EDEMs via sucrose density gradient centrifugation.

As used herein, a "fusogenic moiety" refers to fusogenic lipids or any other fusogenic components of the EDEM or hybridosome. Such a fusogenic moiety enhances or enables the disruption of the membrane, or lipid mixing between a membrane and a lipid bilayer. For example, the first membrane may be from the EDEM while the second membrane encompasses the BDM. Alternatively, the first membrane may be the one of the hybridosome while the second membrane is an outer cell surface membrane, an endosomal membrane, a lysosomal membrane or a nuclear membrane. The fusogenic moiety increase the interaction of the EDEM or of the hybridosome comprising said fusogenic moiety with a second membrane, thereby promoting the mixing of the membrane lipids and the mixing of the internal volume and encapsulated contents. Alternatively, fusogenic moiety may increase the entry into, or exit from, a cellular compartment. Such compartments can be, for instance, endosomes or the nucleus. In certain embodiments the fusogenic moiety may be for example a targeting factor such as a membrane-disruptive synthetic polymer, or for example, a pH responsive membrane translocating polypeptide (e.g. Melittin). In some embodiments the fusogenic moiety can comprise a fusogenic segment (e.g., the head group of a lipid, the tail group of a lipid, block or region of a polymer, a segment of a peptide).

By the term "tunable" as used herein, it is meant that by varying the reaction conditions (e.g. pH, temperature, salts) of the method of the present invention and/or by varying the amounts of the fusogenic components (e.g. ionizable lipids, fusogenic lipid, pH-responsive polymer, helper lipids, fusogenic targeting moiety) of the EDEM, it is possible to selectively grant high fusogenic properties to the EDEM and/or BDM during the uniting reaction while maintaining a lower relative fusogenicity prior or post uniting. Preferably, in each case, the fusogenic moiety can have tunable fusogenicity at a desired quantity (e.g., concentration) thereof. A fusogenic characteristic of a fusogenic moiety can be determined by suitable assays known in the art. For example, fusogenicity of a polymer can be determined in an in vitro cell assay such as the red blood cell hemolysis assay. An endosomolytic polymer activity can be determined in an in vitro cell assay.

The term "fusogenic lipid" may be used to refer to lipids which undergo a change in structure and/or charge at low pH (i.e. pH of about 5.5), when compared to their charge or structure at high pH (i.e. pH of about 7.4), which results in the lipid becoming more fusogenic. These fusogenic lipids may be anionic lipids, neutral lipids or pH sensitive lipids which are characterized in that when the pH is changed from approximately pH 7 to approximately pH 4, the lipid undergoes a change in charge or structure such that it becomes more fusogenic. The change in charge or structure may also occur vice versa from an approximate pH of 4 to approximately 6. In other embodiments, when the temperature is raised above the phase transition temperature, for example 20° C., the fusogenic lipid undergoes a change in structure such that it assumes a hexagonal or cone-forming structure. Additional fusogenic lipids of this type are known in the art and may be used in the formulations, complexes and methods described herein. Some examples of these "fusogenic" lipids change structure to adopt a hexagonal structure, while other examples of these lipids undergo a change in charge. These fusogenic lipids may also include those referred to as "cone-forming" lipids in the art. The term "fusogenic lipid" may also be used to refer to lipids that exhibit molecular shape properties of cone formation such that the lipid framework comprises a small cross sectional head group and a larger acyl chain cross-sectional area. Without wishing to be bound by any specific theory, above a specific temperature (e.g. 20° C.) these lipids are thought to induce a non-bilayer hexagonal $H_{II}$ phase transition.

As used herein, the terms "lipid" and "lipoid" refer to a group of organic compounds that comprise a polar headgroup which is bound to a lipophilic tail-group by way of a linker group. Lipids are generally characterized by being insoluble in water but soluble in many organic solvents. Lipids are usually divided in at least three classes: "simple lipids" which include fats and oils; "compound lipids" which include phospholipids and glycolipids; and "derived lipids" such as steroids. The term "lipid" and "lipoid" may be used interchangeably.

As used herein, "helper lipid" refers to stabilizing lipids, including neutral lipids and anionic lipids. Some EDEMs used in the present invention comprise or may be enriched with one or more helper lipids, such as cholesterol and 1,2-distearoyl-sn-glycero-3-phosphocholine (DSPC). A neutral lipid refers several lipid species that exist in either an uncharged or neutral zwitterionic form at physiological pH. Representative lipids include, but are not limited to, distearoyl-phosphatidylcholine (DSPC), dioleoyl-phosphatidylcholine (DOPC), dipalmitoyl-phosphatidylcholine (DPPC), dioleoyl-phosphatidylglycerol (DOPG), dipalmitoyl-phosphatidylglycerol (DPPG), dioleoyl-phosphatidylethanolamine (DOPE), palmitoyloleoyl-phosphatidylcholine (POPC), palmitoyloleoyl-phosphatidylethanolamine (POPE) and dioleoyl-phosphatidy-lethanolamine, dipalmitoyl-phosphatidyl-ethanolamine (DPPE), dimyristoylphospho-ethanolamine (DMPE), distearoyl-phosphatidyl-ethanolamine (DSPE), 16-O-monomethyl PE, 16-O-dimethyl PE, 18-1-trans PE, 1-stearioyl-2-oleoyl-phosphatidyethanol amine (SOPE), and 1,2-dielaidoyl-sn-glycero-3-phophoethanolamine (transDOPE). An anionic lipid is a lipid that is negatively charged at physiological pH. These lipids include phosphatidylglycerol, diacylphosphatidylserine, cardiolipin and neutral lipids modified with anionic modifying groups.

As used herein, an "ionizable cationic lipid" refers to a lipid that carries a net positive charge at a selected pH (e.g. below physiological pH). Such lipids include, but are not limited to, 1,2-DiLinoleyloxy-N,N-dimethylaminopropane (DLinDMA), 2,2-dilinoleyl-4-(2-dimethylaminoethyl)-[1,3]-dioxolane (DLin-KC2-DMA), heptatriaconta-6,9,28,31-tetraen-19-yl4-(dimethylamino)butanoate (DLin-MC3-DMA), dioctadecyl-dimethylammonium (DODMA), Distearyldimethylammonium (DSDMA), N,N-dioleyl-N,N-dimethyl-ammonium chloride (DODAC); N-(2,3-dioleyloxy)propyl)-N,N,N-trimethyl-ammonium chloride (DOTMA); 1,2-dioleoyl-3-dimethylammonium-propane (DODAP), N-(4-carboxybenzyl)-N,N-dimethyl-2,3-bis(oleoyloxy)propan-1-aminium (DOBAQ), YSK05, 4-(((2,3-bis(oleoyloxy)propyl)-(methyl)amino)methyl)benzoic acid (DOBAT), N-(4-carboxybenzyl)-N,N-dimethyl-2,3-bis(oleoyloxy)propan-1-aminium (DOBAQ), 3-((2,3-bis(oleoyloxy)propyl)(methyl)amino)propanoic acid (DOPAT), N-(2-carboxypropyl)-N,N-dimethyl-2,3-bis-(oleoyloxy)-propan-1-aminium (DOMPAQ), N-carboxymethyl)-N,N-dimethyl-2,3-bis(oleoyloxy)propan-1-aminium (DOAAQ), Alny-100, 3-(dimethylamino)-propyl(12Z,15Z)-3-[(9Z,12Z)-octadeca-9,12-dien-1-yl]-henicosa-12,15-dienoate (DMAP-BLP) and 3-(N-(N',N'-dimethylaminoethane)-carbamoyl)cholesterol (DC-Chol).

In some embodiments the ionizable cationic lipid may be an amino lipid. As used herein, the term "amino lipid" is meant to include those lipids having one or two fatty acid or fatty alkyl chains and an amino head group (including an alkylamino or dialkylamino group) that may be protonated to form a cationic lipid. In certain embodiments, amino or cationic lipids of the invention have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that the entire lipid be present in the charged or neutral form. Lipids that have more than one protonatable or deprotonatable group, or which are zwitterionic, are not excluded from use in the invention.

In one embodiment, the cationic lipid may be synthesized by methods known in the art and/or as described in International Publication Nos. WO2012040184, WO2011153120, WO2011149733, WO2011090965, WO2011043913, WO2011022460, WO2012061259, WO2012054365, WO2012044638, WO2010080724 WO201021865 and WO2014089239; as well as US Publication Nos. US20140309277; each of which is herein incorporated by reference in their entirety.

It should be noted that the term "ionizable" refers to a compound having at least one ionizable site in its molecular structure, and does not necessarily mean "ionized," i.e., the ionizable cationic lipid may be in either ionized or unionized form. In some specific embodiments, the EDEMs used in the present invention comprise a combination of ionizable cationic lipids disclosed above (e.g., DLinDMA, DLin-KC2-DMA and/or DLin-MC3-DMA) so as to precisely tailor the net cationic surface charge of the hybridosomes at physiological pH.

The term "pH-responsive polymer" refers to a polymer that at low pH undergoes a change in structure or charge, when compared to their charge or structure at physiological pH (pH of about 7.4), which results in the polymer becoming more fusogenic. In some non-limiting embodiments of the invention the polymers can be made of homopolymers of alkyl acrylic acids, such as butyl acrylic acid (BAA) or propyl acrylic acid (PAA), or can be copolymers of ethyl acrylic acid (EAA). Polymers of alkyl amine or alkyl alcohol derivatives of maleic-anhydride copolymers with methyl vinyl ether or styrene may also be used. In some embodiments, the polymers can be made as copolymers with other monomers. The addition of other monomers can enhance the potency of the polymers, or add chemical groups with useful functionalities to facilitate association with other molecular entities, including the targeting moiety and/or other adjuvant materials such as poly(ethylene glycol). These copolymers may include, but are not limited to, copolymers with monomers containing groups that can be cross-linked to a targeting moiety.

In general, the pH-responsive polymer is composed of monomeric residues with particular properties. Anionic monomeric residues comprise a species charged or chargeable to an anion, including a protonatable anionic species. Anionic monomeric residues can be anionic at an approximately neutral pH of 7.2-7.4. Cationic monomeric residues comprise a species charged or chargeable to a cation, including a deprotonatable cationic species. Cationic monomeric residues can be cationic at an approximately neutral pH of 7.2-7.4. Hydrophobic monomeric residues comprise a hydrophobic species. Hydrophilic monomeric residues comprise a hydrophilic species.

Generally, each polymer can be a homopolymer (derived from polymerization of one single type of monomer—having essentially the same chemical composition) or a copolymer (derived from polymerization of two or more different monomers—having different chemical compositions). Polymers which are copolymers include random copolymer chains or block copolymer chains (e.g., diblock copolymer, triblock copolymer, higher-ordered block copolymer, etc.). Any given block copolymer chain can be conventionally configured and effected according to methods known in the art. Generally, each polymer can be a linear polymer, or a non-linear polymer. Non-linear polymers can have various architectures, including for example branched polymers, brush polymers, star-polymers, dendrimer polymers, and can be cross-linked polymers, semi-cross-linked polymers, graft polymers, and combinations thereof.

As used herein, the term "unite", "uniting", "unification" or "fusion" refers to a direct interaction between the membrane and/or constituents of the membrane of one or more EDEMs and BDMs. The term "direct interactions" may refer to simple aggregation, lipid exchange, structural rupture, hemifusion and fusion. The terms "hemifusion" and "fusion" refer to the partial or complete mixing of the components of the membranes of the BDM and EDEM and the formation of a common internal space comprising the material originally contained in each of the BDMs/EDEMs forming the fused particle (e.g., active agent, endogenous protein or nucleic acid). The term "fusion efficiency" refers to the relative amount of hybridosomes generated from EDEMs and BDMs which are subject to fusion.

As used herein, the term "membrane" refers to a "shell" comprising aliphatic molecules such as fatty acid, lipid molecules or polymers and encloses an internal compartment. As such, this term may be used to define the membrane of a lipid nanoparticle, of a polymersome, of a naturally secreted particle, or of any type of cell, including bacterial, fungus, plant, animal or human cells (e.g. epithelial cells). The term membrane also includes intracellular lipid bilayers such as for example endosomal or lysosomal membranes as well as nuclear membranes.

The inventor has surprisingly found that the hybridosome of the invention present several advantages over the other pharmaceutical carriers known in the art, which are obtained by physically uniting EDEMs with BDMs and synergizing the advantages displayed by each of these modules. On the one hand, EDEMs can be designed to have precisely defined physicochemical properties, tunable fusogenicity, high encapsulation efficiencies for a wide range of active agents, withstand harsh environments needed for conjugation chemistry and meet clinical manufacturing requirements. On the other hand, BDMs have safe toxicity and immunogenicity profiles, show innate specificity for a target (e.g. a cell, tissue or organ) and are optimized with regard to organism circulation properties. Therefore, the hybridosome of the invention is of particular interest for therapy, imaging and diagnostic applications. A wide variety of active agents may be easily encapsulated in vitro into EDEMs, and by uniting said EDEMs with specific BDMs originating from the subject, a personalized biocompatible hybridosome including the active agents is generated. The hybridosome of the invention may also present one or more of the following advantages: (a) a reduction of sequestration from the macrophages of the reticuloendothelial system (RES); (b) a reduction of the immune system response; (c) an increased circulation lifetime; (d) the delivery with specific and enhanced targeting; and (e) an increase in therapeutic and/or monitoring effects.

Advantageously, the dimensions of the hybridosome of the invention may be tailored so as to fit very specific and targeted applications. Accordingly, in some embodiments of the present invention, specific structural characteristics of the EDEMs and BDMs used to produce the hybridosome may be selected so as to facilitate the distribution of the hybridosome into target tissues. For instance, in order to target solid tumor tissues, one or more of the basic modules (EDEM or BDM) may be selected so that the dimensions of the resulting hybridosome are smaller than fenestrated gaps found in the "leaky" vasculature in solid tumors. In that way, this tailored hybridosome can readily extravasate through fenestrations of the vasculature and directly target the tumor cells from the interstitial space. Similarly, in order to target hepatocytes, one or more of the basic modules may be selected/engineered so that the resulting hybridosome is smaller than the fenestrations of the endothelial layer lining hepatic sinusoids in the liver. In that way, the hybridosome would be able to easily penetrate the endothelial fenestrations to reach the targeted hepatocytes. Conversely, the hybridosome of the invention may be designed in such a way that its dimensions will limit or avoid its distribution to certain cells or tissues. In some specific embodiments, the hybridosome has a size comprised between 20 and 800 nm, preferably between 50 and 400 nm, and more preferably between 100 and 200 nm.

In some specific embodiments, the BDM and/or the EDEM used to generate the hybridosome comprises one or more of receptor-mediated endocytosis, clathrin-mediated and caveolae-mediated endocytosis, phagocytosis and macropinocytosis, fusogenicity, endosomal or lysosomal disruption and/or releasable properties that afford such hybridosomes advantages relative to other similarly classified delivery systems.

The cytotoxicity and/or biocompatibility of the EDEM used in the present invention are reduced by specifically selecting the lipids comprised in its lipid bilayer(s), thereby further enhancing the biocompatibility of the resulting hybridosome. Therefore, EDEM used in the present invention lacks toxic transfection lipids such as Lipofectamine and HiPerFect, which are advantageously replaced by one or more ionizable cationic lipids such as DLinDMA, DLin-KC2-DMA and/or Dlin-MC3-DMA. The ionizable cationic lipids may be used as the sole ionizable lipid of the EDEM (e.g., iLNPs) or may be combined with helper lipids and/or PEG-modified lipids.

As mentioned above, using EDEMs as one component of the hybridosome of the invention offers substantial advantages: (1) EDEMs can be produced by large-scale methods and substantial quantities of encapsulated active agent(s) may be produced; (2) the efficiency of active agent encapsulation is high; (3) the size of the manufactured EDEMs may be controlled so that the resulting hybridosomes can be produced with a therapeutically optimal size; (4) due to fact that EDEMs are produced in vitro, some specific structural characteristic may be maintained in order to ease the separation of non-united subpopulations; (5) EDEMs are able to withstand harsh environments needed for conjugation chemistry; and (6) EDEMs used in the invention have a tunable fusogenicity. As several EDEMs may be united with one or more BDMs, it may be possible to separately generate EDEMs encapsulating distinct active agents (that could not be encapsulated together for some reasons, such as different solubility in solvent etc.) and then unite each of said distinct EDEMs to one or more BDMs, thereby generating a hybridosome comprising all the desired active agents.

In some particular embodiments, the EDEM used in the invention is modified with a targeting moiety and/or a stabilizing moiety.

EDEMs used in the present invention display enhanced physical and chemical stability compared to BDM subunits. Accordingly, while BDMs show good stability in a physiological environment, EDEMs are able to withstand the versatile environments required for conjugation chemistry and post insertions. For example, EDEMs may preserve stability when in contact with reduction agents (e.g. dithiothreitol (DTT)). In conjunction with this enhanced stability, the present invention contemplates the modification of EDEM surfaces by use of additional excipients. In one embodiment, the term "modified" may be used to characterize a modified EDEM relative to the manufactured EDEM from which that modified EDEM was prepared. Accordingly, "modified" may also refer to changes in EDEM formulations as EDEM compositions of the present invention may be enriched with fusogenic moieties or additional cationic, non-cationic and PEG-modified lipids to further target tissues or cells.

The EDEMs used in the present invention may be prepared to impart preferential targeting of the hybridosomes to specific tissues, cells or organs, such as the heart, lungs, kidneys and/or brain. For example, EDEMs such as iLNPs may be prepared to achieve enhanced delivery to the target cells and tissues.

As used herein, "targeting moieties" are excipients that may be bound (either covalently or non-covalently) in vitro to the EDEM to encourage interaction of the hybridosome with certain target cells or target tissues. As used in this disclosure, "bound" or "conjugated" means two entities (here a targeting moiety and a carrier vesicle) are associated with sufficient affinity that the therapeutic/diagnostic benefit of the association between the two entities is realized. For example, targeting may be mediated by the inclusion of one or more targeting ligands (e.g. monoclonal antibody) within or on the hybridosome to encourage delivery to the target cells or tissues. Recognition of the targeting ligand by the targeted tissues actively facilitates tissue distribution and cellular uptake of the content of the hybridosome by the target cells and tissues. Suitable ligands are selected based upon their physical, chemical or biological properties (e.g., selective affinity and/or recognition of target cell surface markers or features).

Targeting ligands are selected such that the unique characteristics of a target cell are exploited, thus allowing the hybridosome to discriminate between target and non-target cells. Such targeting moieties can include, but are not limited to, any member of a specific binding pair, antibodies, monoclonal antibodies as well as derivatives or analogues thereof, including variable domain (Fv) fragments, single chain Fv (scFv) fragments, Fab' fragments, F(ab')$_2$ fragments, single domain antibodies; antibody fragments, humanized antibodies, antibody fragments; multivalent versions of the foregoing.

Contemplated are hybridosomes that comprise one or more ligands (e.g., peptides, aptamers, oligonucleotides, a vitamin or other molecules) that are capable of enhancing the affinity of the compositions to one or more target cells or tissues. In some embodiments, the targeting ligand may span the surface of a lipid nanoparticle (e.g. a glycosaminoglycan) be embedded or be encapsulated within the hybridosome. In one embodiment, hybridosomes include multivalent binding reagents including without limitation: monospecific or bispecific antibodies, such as disulfide stabilized Fv fragments, scFv tandems ((SCFV)2 fragments), diabodies, tribodies or tetrabodies, which typically are covalently linked or otherwise stabilized (i.e. leucine zipper or helix stabilized) scFv fragments; and other homing moieties include for example, aptamers, receptors, and fusion proteins.

In some embodiments, the hybridosome can be utilized for multi-specific affinity regimes. Hereby the hybridosome comprises at least two distinct targeting moieties covalently linked to the hybridosome surface. The first targeting moiety specifically binds to an antigen or molecule on the cell surface (i.e. cell surface antigen), and the second targeting moiety binds to an intracellular target. In some embodiments, the first targeting moiety and the second targeting moiety are included in a single polypeptide chain. In certain embodiments, some or all of a targeting moiety is composed of amino acids (including natural, non-natural, and modified amino acids), nucleic acids and aptamer or saccharides. In certain embodiments, a targeting moiety is a small molecule. In some embodiments the intracellular targeting moiety is exogenous and conjugated to the EDEM while the extracellular targeting moiety is present on the BDM and produced in vivo. In another embodiment, the intracellular targeting moiety generated in vivo is present on the BDM while an extracellular targeting moiety is conjugated to the EDEM.

The "first targeting moiety" in a bispecific embodiment may be an antibody, antibody-like molecule, peptide, or a small molecule, such as vitamins, e.g., folate, sugars such as lactose and galactose, or other small molecules. The cell surface antigen may be any cell surface molecule that undergoes internalization, such as a protein, sugar, lipid head group or other antigen on the cell surface. Examples of cell surface antigens useful in the context of the present invention include but are not limited to the tetraspanins, the EGF receptor, HER2/Neu, VEGF receptors, integrins, CD38, CD33, CD19, CD20, CD22 and the asialoglycoprotein receptor.

The "second targeting moiety" in a bispecific embodiment recognizes an intracellular target. This targeting moiety binds specifically to an intracellular membrane surface or antigen, such as a protein. In certain embodiments, an intracellular targeting moiety will enhance the localization of a substance to desired intracellular location. In some embodiments, the second targeting moiety is proteinaceous, and in certain embodiments is an antibody or antibody-like molecule. Other second targeting moieties include peptides, such as for example the synthetic melittin peptide analogues, and organic macromolecules which by virtue of their size (a molecular weight of >500 g), charge, or other physicochemical properties, are unable or poorly able to enter cells independently. In some embodiments, the second targeting moiety is a nucleic acid aptamer. The second targeting moiety may bind to cytosolic proteins; proteins bound to the inner face of the plasma membrane, or the nuclear, mitochondrial or other membranes in the cell; or nuclear proteins or proteins in other subcellular compartments. It will be evident to those skilled in the art that targeting moiety which blocks critical functions of intracellular signaling will be good candidates for use as second targeting moieties. Second targeting moieties may directly inhibit the activity of a protein, or block an interaction with a protein's substrate, or they may block protein-protein interactions.

A further embodiment encompasses the incorporation of complementary functional targeting moieties for the enhancement of active hybridosome intracellular transport. An example for enhanced intracellular transport is achieved by employing targeting moieties capable of "hijacking", binding or engaging natural active cellular transport systems. For example, binding one of these proteins of the microtubule motor complex with a motor protein-binding peptide allows for active transport along the microtubule transport network. Exemplary motor proteins include, but are not limited, to dynein and kinesin.

In certain embodiments, the second targeting moiety possesses a dual role, namely membrane penetrating capacities and intracellular targeting functionalities. For example the peptide melittin or analogues thereof possess a membrane interaction ability at low pH and a nuclear-homing functionality within the cytosol. This dual role maybe attributed to a segment of the second targeting moiety. For example, nuclear targeting functions mediated through nuclear localization sequences (e.g. peptide sequence "KRKR") and amphipathic α-helix segments contained within the same second targeting moiety. Hence, in certain embodiments the dual role of a second targeting moiety can mediate two complementary functions to the hybridosome. Exemplary hybridosome compositions modified with dual-purpose second targeting moiety is described in the Examples below.

Furthermore the EDEMs of the invention could be modified to exhibit molecules with amphipathic properties such as cell-penetrating peptides on their surface. These peptides are characterized by their capacity to disturb membrane bilayer integrity, either by creation of defects, disruption, or through pore formation, leading to an interaction between EDEMs and BDMS. Examples of such peptides can be derived from proteins such as Tat and Rev as well as peptides derived from toxins such as crotamine or melittin. A preferred class of cell-penetrating peptides suitable for use within the present invention include hydrophobic domains that are "inert" at physiological pH, but are active in the low pH environment. Upon pH-induced unfolding and exposure of the hydrophobic domain, the moiety binds to lipid bilayers and effects the interaction between EDEMs and BDMs or hybridosomes and endosomal compartments. Exemplary conjugation of a fusogenic peptide is described in the Examples below.

Contemplated by the present invention is also the incorporation of chemoselective and bio-orthogonal complementary functional molecules into or onto EDEMs to enhance site specific uniting with BDMs. For example, incorporation of fusion peptides into the EDEM lipid bilayer, such as SNARE proteins (soluble N-ethyl maleimide sensitive factor attachment protein receptors) or synthetic mimics thereof, allow for a receptor specific interaction between EDEMs and BDMs.

In one embodiment, to facilitate the conjugation of targeting moieties to the EDEM, a portion of the molar ratio of PEG-modified lipid may be substituted for PEG-modified lipids with a functional entity such as a maleimide (e.g. 1,2-distearoyl-sn-glycero-3-phosphoethanolamine-N-[maleimide(polyethylene glycol)-2000]) or an amine group (e.g. 1,2-distearoyl-sn-glycero-3-phosphoethanolamine-N-[amino(polyethylene-glycol)-2000]) at the distal end of the PEG. Exemplary conjugation methods are described in the Examples below.

EDEMs described herein may further comprise a shielding moiety anchored into the lipid bilayer. As used herein, the term "stabilizing moiety" refers to a molecule that can modify the surface properties of the hybridosome through the EDEM component included therein. A stabilizing moiety can prevent the hybridosome from sticking to each other or sticking to blood cells or vascular wails. In certain embodiments, hybridosomes with stabilizing moieties have reduced immunogenicity when they are administered to a subject. In one embodiment, stabilizing moieties can also increase blood circulation time of the hybridosomes within a subject. Stabilizing moieties for use in the present invention can include those generally well known in the art.

Examples of stabilizing moieties include but are not limited to compounds comprising polyethylene glycol and other compounds such as, but are not limited to, dendrimers, polyalkylene oxide, polyvinyl alcohol, polycarboxylate, polysaccharides, and/or hydroxyalkyl starch, which reduce the interaction or binding of the complex to species present in vivo or in vitro, such as serum complement protein, co-factors, hormones or vitamins. The term "PEG-modified lipid" refers to but is not limited to, a polyethylene glycol chain of up to 20 kDa in length, covalently conjugated to a lipid with alkyl chain(s) of C6-C20 length. In certain embodiments, suitable polyethylene glycol-lipids include PEG-modified phosphatidylethanolamine (PEG-PE), PEG-modified ceramides (e.g. PEG-CerC20), PEG-modified dialkylamines, PEG-modified diacylglycerols and PEG-modified dialkylglycerols. In one embodiment, the polyethylene glycol-lipid is (Methoxy Polyethylene Glycol)2000-dimyristolglycerol (PEG-s-DMG). Further non-limiting examples of PEG-modified lipids include PEG-dialkyloxypropyl (DAA), R-3-[(ω-methoxy-poly(ethylene glycol) 2000)carbamoyl)]-1,2-dimyristyloxypropyl-3-amine (PEG-c-DOMG) and N-Acetylgalactosamine-UR)-2,3-bis(octadecyloxy)propyl-I-(methoxy poly(ethylene glycol)2000)propylcarbamate)) (GalNAc-PEG-DSG).

The invention contemplates that provided PEG is displayed on the surface of the EDEM, BDM and/or hybridosomes, compounds other than lipids, such as, for example, peptides, hydrophobic anchors or polymers, carbohydrates, metals or other ions may be used for conjugating with PEG to anchor these compounds into the lipid bilayer.

Turning to BDMs, the present invention contemplates that bioactive molecules in the cytosol and plasma membrane are incorporated during the genesis of BDMs, resulting in BDMS having unique functional properties that allow the BDMs to be utilized as effective nanoparticle carriers of active agents. In this regard, BDMs are able to deliver an active agent to target cells and tissues, while retaining the biological activity of endogenous cargo as well as the active agents. In particular, BDMs show evolutionarily optimized serum half-life and interaction with target tissues and/or cells. The advantageous delivery capability of one or more BDMs is transferred to the hybridosome of the invention after uniting BDMs with one or more EDEMs. Furthermore, BDMs are able to transfer endogenous bioactive components to the hybridosome. In one specific embodiment, one or more BDMs are collected and used to promote the release of endogenous miRNA, polynucleotides and polypeptides produced in vivo by donor cells, into the volume enclosed by the hybridosome of the invention. In another embodiment, one or more BDMs are collected and used to promote the transfer of bioactive molecules and/or polypeptides embedded in the BDM membrane as constituents of the membrane of the hybridosome.

In some embodiments, the BDMs used in the invention are derived from a donor subject suffering from a disease or a disorder, such as cancer. Without being bound by any particular theory, it is expected that at least some of the BDMs collected from the subject have the capability of specifically targeting the cells associated with said disease or disorder, and therefore may be advantageously used for monitoring or treating the disease. Furthermore, components of the BDMs used in the invention can interact with specific cells and facilitate endocytosis, thereby enabling targeted delivery of encapsulated material to a specific cell, cell type, or tissue. Without being bound by any particular theory, the target cell specificity of BDMs used in the invention depends on the cell type from which the BDM is derived. For instance, BDMs derived from B-cells or Glioblastoma cells may be used to produce the hybridosomes of the invention. Such BDMs may transfer one or more endogenous B-cell or Glioblastoma targeting moieties produced in vivo to the hybridosome, thereby rendering the hybridosome B-cell or glioblastoma specific. Also, it is expected that hybridosome reintroduced into the subject from whom the BDM used to produce the hybridosome is derived, the BDM components transferred to the hybridosome render it compatible with the immune system of said subject.

In some embodiments the cell from which the BDM is derived is a tumor cell. The tumor cell can be a primary tumor cell, or can be produced from a tumor cell e.g. by passaging, culture, expansion, immortalization, etc. Thus the tumor cell may be from a tumor in a cancer or pre-cancer patient, or may be from a tumor or cancer cell line. The tumor cell can be from a benign tumor or a malignant tumor.

In other embodiments, the cell from which the BDM is derived is an infected cell, i.e. a cell that contains a pathogen.

In other embodiments, the cell from which the BDM is derived is a mutated cell. For example, in some embodiments the mutated cell expresses mutant or misfolded proteins. In some embodiments, the mutated cell overexpresses one or more proteins. In some embodiments the mutant cell is involved in a degenerative disorder, such as a proteopathic disorder. In some embodiments, the cell is a central nervous system cell.

In one embodiment, the pharmaceutical composition of the invention comprises a hybridosome which does not contain any therapeutic agents and/or diagnostic agents in its internal compartment. Such a hybridosome may be produced for instance by uniting an "empty" EDEM with a BDM. In some particular embodiments, the "empty" EDEM comprises some structural element in its membrane that would ease further loading of active agents via technique known in the art (e.g. electroporation).

As used herein, "active agent" or "bioactive agent" refers to any compound or mixture of compounds which produces a physiological result, e.g., a beneficial or useful result, upon contact with a living organism, e.g., a mammal, such as a human. Active agents are distinguishable from other components of the delivery compositions, such as carriers, diluents, binders, colorants, etc. The active agent may be any molecule, as well as binding portion or fragment thereof, that is capable of modulating a biological process in a living subject. In certain embodiments, the active agent may be a substance used in the diagnosis, treatment, or prevention of a disease or as a component of a medication. In some embodiments, an active agent may refer to a compound that facilitates obtaining diagnostic information about a targeted site in a body of a living organism, such as a mammal or in a human. For example, imaging agents may be classified as active agents in the present invention as they are substances that provide imaging information required for diagnosis.

In some other embodiments, the hybridosome of the composition comprises one or more therapeutic agents and/or diagnostic agents. As described above, these therapeutic agents and/or diagnostic agents are first encapsulated within an EDEM and then transferred to the internal compartment of the hybridosome by uniting said EDEM with a BDM.

As used herein, a "therapeutic agent" is a physiologically or pharmacologically active substance that can produce a desired biological effect in a targeted site in an animal, such as a mammal or in a human. The therapeutic agent may be any inorganic or organic compound. A therapeutic agent may decrease, suppress, attenuate, diminish, arrest, or stabilize the development or progression of disease, disorder, or cell growth in an animal such as a mammal or human. Examples include, without limitation, peptides, proteins, nucleic acids (including siRNA, miRNA and DNA), polymers, and small molecules. In various embodiments, the therapeutic agents may be characterized or uncharacterized.

In one embodiment, a therapeutic agent may be present in the EDEM or the BDM prior to uniting the two. For example BDMs may contain one or more therapeutic agents (e.g. miRNA) endogenous to the cell from which the BDM is derived and EDEMs may comprise one or more therapeutic agents (e.g. anti-neoplastic agent) prior to uniting with a BDM. Methods for encapsulating active agents into EDEMs are known in the art (Bao, Mitragotri, & Tong, 2013). Alternatively, a hybridosome may be loaded with a therapeutic agent after uniting EDEMs and BDMs, by means of covalent and non-covalent binding to the cell surface, post-insertion into the hybridosome membrane or via opening pores into the membrane of the hybridosome to allow active agents to enter the encapsulated volume (e.g. electroporation).

Therapeutic agents of the present invention may also be in various forms. Such forms include, without limitation, unchanged molecules, molecular complexes, and pharmacologically acceptable salts (e.g., hydrochloride, hydrobromide, sulfate, phosphate, nitrite, nitrate, borate, acetate, maleate, tartrate, oleate, salicylate, and the like). In some embodiments, therapeutic agents can be modified with salts of metals, amines or organic cations (e.g., quaternary ammonium). Derivatives of drugs, such as bases, esters and amides can also be used as a therapeutic agent. A therapeutic agent that is water insoluble can be used in a form that is a water soluble derivative thereof, such as a base derivative. In such instances, the derivative therapeutic agent may be converted to the original therapeutically active form upon delivery to a targeted site. Such conversions can occur by various metabolic processes, including enzymatic cleavage, hydrolysis by the body pH, or by other similar processes.

As contemplated by the invention, suitable therapeutic agents include, without limitation, chemotherapeutic agents (i.e., anti-neoplastic agents), anesthetic agents, beta-adrenaergic blockers, anti-hypertensive agents, anti-depressant agents, anti-convulsant agents, anti-emetic agents, anti-histamine agents, anti-arrhytmic agents, anti-malarial agents, anti-proliferative agents, anti-vascularization agents, wound repair agents, tissue repair agents, thermal therapy agents, and combinations thereof.

In some embodiments, the suitable therapeutic agents can also be, without limitation, immunosuppressive agents, cytokines, cytotoxic agents, nucleolytic compounds, radioactive isotopes, receptors, and pro-drug activating enzymes. The therapeutic agents of the present invention may be naturally secreted or produced by synthetic or recombinant methods, or any combination thereof.

A wide spectrum of therapeutic agents may be used in conjunction with the EDEMs described herein. Non-limiting examples of such therapeutic agents include antineoplastic agents, anti-infective agents, local anesthetics, anti-allergics, anti-anemics, angiogenesis, inhibitors, beta-adrenergic blockers, calcium channel antagonists, anti-hypertensive agents, anti-depressants, anticonvulsants, anti-bacterial, anti-fungal, anti-viral, anti-rheumatics, anthelminithics, anti-parasitic agents, corticosteroids, hormones, hormone antagonists, immunomodulators, neurotransmitter antagonists, anti-diabetic agents, anti-epileptics, anti-hemmorhagics, anti-hypertonics, antiglaucoma agents, immunomodulatory cytokines, sedatives, chemokines, vitamins, toxins, narcotics, plant derived agents (e.g. from leaves, roots, flowers, seeds, stems or branches extracts) and combinations thereof.

In various embodiments, drugs that are affected by classical multidrug resistance can have particular utility as therapeutic agents in the present invention. Such drugs include, without limitation, vinca alkaloids (e.g., vinblastine), the anthracyclines (e.g., doxorubicin) and RNA transcription inhibitors.

In additional embodiments, the therapeutic agent may be a cancer chemotherapy agent. Examples of suitable cancer chemotherapy agents include, without limitation: nitrogen mustards, nitrosorueas, ethyleneimine, alkane sulfonates, tetrazine, platinum compounds, pyrimidine analogs, purine analogs, antimetabolites, folate analogs, anthracyclines, taxanes, vinca alkaloids, and topoisomerase inhibitors and hormonal agents.

Additional cancer chemotherapy drugs that may be used as therapeutic agents in the present invention include, without limitation: alkylating agents, such as cyclosphosphamide; alkyl sulfonates; aziridines; ethylenimines and methylamelamines; anti-metabolites; pyrimidine analogs; anti-adrenals; folic acid replenisher; retinoic acid; and pharmaceutically acceptable salts, acids or derivatives of any of the above.

Additional therapeutic agents that are suitable for use in the present invention include, without limitation, anti-hormonal agents that act to regulate or inhibit hormone action on tumors. Non-limiting examples of such anti-hormonal agents include anti-estrogens, including for example Tamoxifen and Toremifene; anti-androgens, such as Leuprolide and pharmaceutically acceptable salts, acids or derivatives of any of the above.

In additional embodiments of the present invention, cytokines can be also used as therapeutic agents. Non-limiting examples of such cytokines are lymphokines, monokines, and traditional polypeptide hormones. Additional examples include growth hormones, such as human growth hormone, N-methionyl human growth hormone, and bovine growth hormone; parathyroid hormone; thyroxine; insulin; proinsulin; relaxin; prorelaxin; glycoprotein hormones, such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet growth factor; transforming growth factors (TGFs) such as TGF-α and TGF-β; insulin-like growth factor-I and -II; erythropoietin (EPO); osteoinductive factors; interferons, such as interferon-α, -β and -γ; colony stimulating factors (CSFs), such as macrophage-CSF (M-CSF), granulocyte-macrophage-CSF (GM-CSF), and granulocyte-CSF (GCSF); interleukins (ILs); tumor necrosis factors, such as TNF-α or TNF-β; and other polypeptide factors, including LIF and kit ligand (KL). As used herein, the term cytokine includes proteins from natural sources or from recombinant sources (e.g., from T-cell cultures and biologically active equivalents of the native sequence cytokines).

In additional embodiments, the therapeutic agent can also be an antibody-based therapeutic agent, non-limiting examples include Herceptin, Erbitux, Avastin, Rituxan, Simulect, Enbrel, Adalimumab, and Remicade.

In some embodiments, the therapeutic agent can be a nanoparticle. Non-limiting examples of such nanoparticles include any metal and semiconductor based nanoparticle, which includes but is not limited to: gold, silver, iron oxide, quantum dots or carbon nanotubes. For example, in some embodiments, the nanoparticle can be a nanoparticle that can be used for a thermal ablation or a thermal therapy.

In some embodiments, the EDEM is loaded with anionic therapeutic agents. Anionic therapeutic agents include any therapeutic agent with a net negative charge, or having a negatively charged group that is able to interact with an ionizable lipid of the hybridosome. Such therapeutic agents include any known or potential therapeutic agent, including drugs and compounds such as, but not limited to, oligonucleotides, nucleic acids, modified nucleic acids (including protein-nucleic acids and the like), proteins and peptides with negative charge groups, conventional drugs such as plant alkaloids and analogues having negative charge groups, and the like. Therapeutic agents which are not inherently anionic may be derivatized with anionic groups to facilitate their use in the invention. For example, paclitaxel can be derivatized with a polyglutamic acid group.

In one embodiment, the hybridosome comprises negatively charged nucleic acids to be introduced into cells. Non-limiting examples of nucleic acids intended to be used in the present invention are siRNA, micro RNA (miRNA), small or short hairpin RNA (shRNA), guide RNA (gRNA), clustered regularly interspaced short palindromic repeat RNA (crRNA), trans-activating clustered regularly interspaced short palindromic repeat RNA (tracrRNA) immunestimulating oligonucleotides, plasmids, antisense nucleic acids and ribozymes. The present invention contemplates that nucleic acids contained within a hybridosome can be endogenous to the cell the BDM was derived from and/or an exogenous nucleic acid encapsulated by the EDEM.

In some embodiments, polynucleotides encapsulated by the hybridosome encode a small interfering RNA (siRNA) or antisense RNA for the purpose of modulating or otherwise decreasing or eliminating the expression of an endogenous nucleic acid or gene. In certain embodiments, such encapsulated polynucleotides may be natural or recombinant in nature and may exert their therapeutic activity using either sense or antisense mechanisms of action (e.g., by modulating the expression of a target gene or nucleic acid). As used herein, the term "modulating" refers to altering the expression of a target polynucleotide or polypeptide. Modulating can mean increasing or enhancing, or it can mean decreasing or reducing.

In some other embodiments, the hybridosome of the invention comprises polynucleotides encoding polypeptides or proteins of interest, such as a hormone, enzyme, receptor, or modulating peptides. In some specific embodiments, the hybridosome comprises bioactive agents that, further to transfection, are able to produce functional polypeptides that may ease the targeting/transfection of further hybridosome to the target cells. In certain embodiments the hybridosomes described herein employ a multifunctional strategy to facilitate the delivery of encapsulated materials (e.g., one or more polynucleotides) and subsequent release when interacting with a target cell.

Typically, a pharmaceutical composition for use as a vaccine for a particular cancer type will comprise BDMs derived from tumor/cancer cells of that particular cancer type. For example, a pharmaceutical composition for use in a glioblastoma cancer vaccine typically comprises BDMs purified from glioblastoma tumor/cancer cells. In this way, the BDM comprises tumor-associated antigens that stimulate an adaptive immune response to antigens present on the tumor/cancer cells to be treated/protected against. The same origin/intent matching applies to other diseases.

In one embodiment, BDMs useful with the invention can be any proteoliposomic vesicle obtained by disruption of or blebbing from a bacterial outer membrane or parasite to form vesicles which retain antigens from the outer membrane (see International Pub No. WO2014122232 and WO201108027, each of which is herein incorporated by reference in their entirety). BDMs derived from bacteria and parasites have a number of properties which make them attractive candidates for immunotherapy delivery platforms including: (i) strong immunogenicity, (ii) self-adjuvanticity, (iii) capability to interact with mammalian cells and be taken up through membrane fusion or cell attachment via adhesion-receptors, and (iv) the possibility of incorporating heterologous antigen expression by recombinant engineering.

A pharmaceutical composition comprising the hybridosome of the invention and at least one pharmaceutically acceptable carrier or excipient may be therefore used for the treatment or prophylaxis of various disease and disorders.

As used herein, "diagnostic agent" refers to a component that can be detected in a subject or test sample and is further described herein. In some embodiments, diagnostic agents in the present invention may be substances that provide imaging information about a targeted site in a body of an animal, such as a mammal or in a human. A diagnostic agent used in the present invention can include any diagnostic agent known in the art.

A diagnostic agent can be detected by a variety of ways, including as an agent providing and/or enhancing a detectable signal that includes, but is not limited to, gamma-emitting, radioactive, optical, fluorescent absorptive, echogenic, magnetic or tomography signals. Techniques for imaging the diagnostic agent can include, but are not limited to, computed tomography (CT), magnetic resonance imaging (MRI), optical imaging, single photon emission computed tomography (SPECT), positron emission tomography (PET), x-ray imaging, gamma ray imaging, and the like.

In one embodiment, a radioisotope can act as a diagnostic agent and be incorporated into the hybridosome described herein and can include radionuclides that emit gamma rays, positrons, beta and alpha particles, and X-rays. Suitable radionuclides include but are not limited to limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{123}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y.

In some embodiments, the payload may be a detectable agent, such as, but not limited to, various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials). Such optically-detectable labels include for example, without limitation, octadecyl rhodamine B, 7-nitro-2-1,3-benzoxadiazol-4-yl, 4-acetamido-4'-isothiocyanatostilbene-2,2' disulfonic acid, acridine and derivatives, 5-(2'-aminoethyl) aminonaphthalene-1-sulfonic acid (EDANS), 4-Amino-N-(3-[vinylsulfonyl]phenyl)naphthalimide-3,6-disulfonate dilithium salt, N-(4-anilino-1-naphthyl)maleimide, anthranilamide, BODIPY, Brilliant Yellow, coumarin and derivatives, cyanine dyes, cyanosine, 4',6-diaminidino-2-phenylindole (DAPI), Bromopyrogallol Red, 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, dansylchloride, 4-dimethylaminophenylazophenyl-4'-isothiocyanate (DABITC), eosin and derivatives, erythrosin and derivatives, ethidium, fluorescein, 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein isothiocyanate, X-rhodamine-5-(and 6)-isothiocyanate (QFITC or XRITC), fluorescamine, ten-1-yl]ethenyl]-1,1-dimethyl-3-(3-sulfopropyl)-, hydroxide, innersalt compound with n,n-diethylethanamine (1:1) (IR144), 5-chloro-2-[2-[3-[(5-chloro-3-ethyl-2(3H)-benzothiazol-ylidene)ethylidene]-2-(diphenylamino)-1-cyclopenten-1-yl]ethenyl]-3-ethyl benzothiazolium perchlorate (IR140), Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene, butyrate quantum dots, Reactive Red 4 (Cibacron™ Brilliant Red 3B-A), rhodamine and derivatives, 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N', N'tetramethyl-6-carboxyrhodamine (TAMRA) tetramethyl rhodamine, tetramethyl rhodamine isothiocyanate (TRITC), riboflavin, rosolic acid, terbium chelate derivatives, Cyanine-3 (Cy3), Cyanine-5 (Cy5), Cyanine-5.5 (Cy5.5), Cyanine-7 (Cy7), IRD 700, IRD 800, Alexa 647, La Jolta Blue, phthalo cyanine, and naphthalo cyanine.

For embodiments involving optical imaging, the diagnostic agent may be contrast agents for example, semiconductor nanocrystals or quantum dots. For optical coherence tomography imaging, the diagnostic agent may be a metal, such as gold or silver nanocage particles. In some embodiments, the diagnostic agent may be metal nanoparticles, such as gold or silver nanoparticles.

In some embodiments, a diagnostic agent can include a magnetic resonance (MR) imaging agent. Exemplary magnetic resonance agents include but are not limited to paramagnetic agents, superparamagnetic agents, and the like. Exemplary paramagnetic agents can include but are not limited to Gadopentetic acid, Gadolinium, Gadoteridol, or Gadoxetic acid. Superparamagnetic agents can include but are not limited to superparamagnetic iron oxide and Ferristene. In certain embodiments, the diagnostic agents can include x-ray contrast agent. Examples of x-ray contrast agents include, without limitation, iopamidol, iomeprol, iohexol, iopentol or metrizamide, Similar to therapeutic agents described above, the diagnostic agents can be associated with the hybridosome in a variety of ways, including for example being embedded in, encapsulated in, or tethered to the hybridosome. In some embodiments, the diagnostic agent may be a metal ion complex/conjugate that can be covalently or non-covalently attached to a particle's surface. In some embodiments, the diagnostic agent may be a radionucleotide that can be covalently or non-covalently attached to a hybridosome's surface. Similarly, loading of the diagnostic agents can be carried out through a variety of ways known in the art. One example of loading diagnostic agents into EDEMs is found in the Examples Section.

Accordingly, one embodiment of the present invention relates to a hybridosome comprising at least one EDEM, which may contain an active agent, such as a diagnostic agent and/or a therapeutic agent. The hybridosome may be used as a part of a composition for treating, monitoring, preventing, staging and/or diagnosing a disease or condition, including a disease, such as cancer. This may be accomplished, for example, by combining a therapeutic agent and a diagnostic agent in the hybridosome. This may also be accomplished by administering a hybridosome that includes a first subpopulation loaded with a therapeutic agent and a second subpopulation loaded with a diagnostic agent. In another embodiment, the invention provides a method for diagnosing a disease or condition diagnosable by administering a diagnostic agent, comprising administering a hybridosome of the invention to a subject in need thereof.

A pharmaceutical composition comprising the hybridosome of the invention and at least one pharmaceutically acceptable carrier or excipient may be therefore used for diagnostic applications.

In a further aspect, the invention provides a pharmaceutical composition comprising a hybridosome wherein active agents incorporated in BDMs elicit an immune towards one or more disease-associated antigens such as for example a tumor antigen. It is contemplated that a pharmaceutical composition comprising a hybridosome capable of eliciting an immune response may be useful in the context of immunotherapy, for example against cancer or infections.

In some embodiments the BDMs comprise in vivo generated disease-associated antigens, such as one or more tumor associated antigen, one or more pathogen-associated antigen or one or more degenerative-disorder-associated antigen. The term "disease-associated antigens" can relate to proteins produced in disease associated cells that have an abnormal structure and/or an abnormal expression pattern compared to non-disease associated cells. Abnormal proteins are also produced by cells infected with oncoviruses, e.g. EBV and HPV. For example, in some embodiments, the BDMs are well-suited for presenting antigens that can stimulate desirable immune responses in subjects. This advantage may arise because BDMs are produced by cells, rather than artificially-synthesized, and therefore provide antigens that are "natural". That is, the antigens produced by the cells and found in the BDMs can be full-length peptides that are processed (e.g., glycosylated, etc.) and folded by the cell to a similar extent as antigens experienced by immune cells in a subject. In addition to proteins, other substances like cell surface glycolipids and glycoproteins may also have an abnormal structure in disease associated cells and could thus be targets of the immune system. As such, the BDM antigens may be utilized in vaccines or treatments against, for example cancers. In some embodiments, therefore, the one or more antigens can each comprise a cancer cell antigen. As non-limiting examples, the cancer cell antigen can be placental type alkaline phosphatase, p53, p63, p73, mdm-2, procathepsin-D, B23, C23, PLAP, CA125, MUC-1, cerB/HER2, NY-ESO-1.SCP1, SSX-1, SSX-2, SSX-4, HSP27, HSP60, HSP90, GRP78, TAG72, HoxA7, HoxB7, EpCAM, ras, mesothelin, survivin, EGFK, MUC-1, and c-myc.

In another embodiment, BDMs are derived from antigen presenting cells. The invention particularly contemplates BDMs derived from diseased antigen presenting cells. In a specific embodiment, the BDMs comprise tumor associated antigens from chronic lymphocytic leukemia (CLL) and mantle cell lymphoma. In a non-limiting example, BDMs are derived from mantle cell lymphoma cells which bear the Tyrosine-protein kinase transmembrane receptor ROR1.

In a further aspect, the invention provides a pharmaceutical composition comprising a hybridosome wherein active agents incorporated in BDMs elicit immune suppression capabilities to the composition as, for example desired in the context of autoimmune diseases, infections, allergies and transplantation to avoid detrimental activation and/or overreaction of a subjects' immune system. This aspect can be realized by isolating BDMs presenting one or more immunosuppressing agents. In one embodiment said BDMs inhibit immune reaction developing as result of allogeneic/xenogeneic cell transplant or gene therapy. As shown in the Examples Section, one embodiment includes immunosuppressive BDMs isolated from thrombocytes and activated polymorphonuclear neutrophils.

In a further aspect, the invention provides a pharmaceutical composition comprising a hybridosome for the delivery of therapeutic agents.

As used herein, "pharmaceutical composition" refers to a composition comprising physically discrete units to be administered in single or multiple dosages, each unit containing a predetermined quantity of at least one pharmaceutically active ingredient, and at least one other ingredient selected from pharmaceutically acceptable excipients. For instance, the present invention provides a pharmaceutical composition comprising hybridosomes for the targeted delivery of one or more active agents to a tissue or cell in a living organism. In a further example the present invention provides a pharmaceutical composition comprising hybridosomes for the delivery of one or more active agents to a tissue or cell in vitro.

In some embodiments, the hybridosome of the present invention may be used as systems for the delivery of an active agent, such as a therapeutic and/or diagnostic agent, to a targeted cell or tissue in an animal such as a mammal or in a human being. In certain embodiments, the present invention provides methods for introducing an active agent into a target cell or tissue. The particles of the invention can include a wide variety of therapeutic and/or diagnostic agents. In another aspect, the invention provides a method for administering a therapeutic and/or diagnostic agent to a subject. In the method, a hybridosome of the invention comprising a therapeutic and/or diagnostic agent is administered to the patient in need thereof. In certain embodiments, delivery of an active agent, such as a therapeutic and/or diagnostic agent, may constitute a mean of therapy.

The term "therapy" or "treatment" refers to a process that is intended to produce a beneficial change in the condition of an individual like a mammal, e.g., a human, often referred to as a patient, or animal. A beneficial change can, for example, include one or more of: restoration of function, reduction of symptoms, limitation or retardation of progression of a disease, disorder, or condition or prevention, limitation or retardation of deterioration of a patient's condition, disease or disorder. Such therapy usually encompasses the administration of an active agent by means of a hybridosome, among others.

The term "treating" is art-recognized and includes preventing a disease, disorder or condition from occurring in an living organism, such as a mammal or in a human, which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

As mentioned above, the hybridosome of the present invention may comprise therapeutic agents that can be selected depending on the type of disease desired to be treated. For example, certain types of cancers or tumors, such as leukemia, lymphoma, myeloma, carcinoma and sarcoma as well as solid tumors and mixed tumors, can involve administration of the same or possibly different therapeutic agents.

A person of ordinary skill in the art will also recognize that the hybridosome of the present invention can be used for various purposes. The methods of the present invention have numerous advantages over the methods of the prior art. Methods for treating patients using active agents have been used for a long time. However, in most of the prior art methods, the active agent was usually delivered to the whole human or animal body, without being targeted to a particular site affected by a disease. Thus, in the prior art methods, the active agent is distributed uniformly in the whole organism. One drawback of the prior art methods is that unaffected regions of the human or animal body can also be affected by the active agent. Furthermore, only a small part of the active agent could act in the diseased site.

As contemplated by the invention, a hybridosome improves the likelihood that appropriate amounts of encapsulated materials (e.g., therapeutic agents and/or diagnostic agents) is delivered to target cells or tissues, subsequently minimizing potential systemic adverse effects or toxicity associated with non-united modules or their encapsulated contents. For example, when a EDEM (e.g., a iLNP) comprises or is otherwise enriched with one or more of the ionizable lipids, the phase transition in the lipid bilayer of the one or more target cells may facilitate the delivery of the encapsulated materials (e.g., one or more active agents encapsulated in a lipid nanoparticle) into the target cells. Similarly, in certain embodiments the compounds disclosed herein may be used to prepare hybridosomes that are characterized by their reduced toxicity in vivo. In certain embodiments, the reduced toxicity is a function of the high transfection efficiencies associated with the compositions disclosed herein, such that a reduced quantity of such composition may administered to the subject to achieve a desired therapeutic response or outcome.

The hybridosome of the invention may be designed to facilitate encapsulation and release of encapsulated materials (e.g., one or more active agents) to one or more target cells and/or tissues. For example, when a hybridosome comprises or is otherwise enriched with one or more of fusogenic lipids, the phase transition and potential disruption in the lipid bilayer of one or more target cells may facilitate the delivery of the encapsulated materials (e.g., one or more active encapsulated in a hybridosome).

Similarly, in certain embodiments the incorporation of lipids with ionizable hydrophilic head-groups into EDEMs may serve to promote endosomal or lysosomal release of contents that are encapsulated in the hybridosome. Such enhanced release may be achieved by a proton-sponge mediated disruption mechanism, in which the ability of a compound within the EDEM, can buffer the acidification of the endosome, which in turn promotes osmotic swelling and the disruption of the endosomal or lysosomal lipid membrane and facilitate intracellular release of encapsulated cargo therein into the target cell.

In additional embodiments, the hybridosome of the invention may also provide at least one of the following additional advantages for treatment: (1) an increased circulation time of the delivery system; (2) a mitigated RES uptake of the hybridosome by using patient derived BDMs and optionally adding stabilizing moieties; (3) the prevention of premature release of cargo from within the hybridosome due stable encapsulation; (4) a reduced immune system response when introduced in a body of a subject due to the presence of endogenous BDM components; (5) an increased transcytosis of the hybridosome through the biological barriers (e.g. endothelial barrier, blood-brain barrier) in the vasculature due to endogenous targeting moieties on the BDM or exogenous targeting moieties tethered to the EDEM; (6) an increased accumulation of the hybridosome at a diseased site, such as a tumor site; (7) an increased internalization into endosomes of the target cell due to endogenous targeting moieties originating from the BDM and subsequent endosomal release due to fusogenic properties supplied by the EDEM. As discussed above, in certain embodiments, the hybridosome of the present invention allows for the delivery of an active agent preferentially to a diseased site. Such a targeted delivery may also allow one to avoid high doses of an active agent. Such a targeted delivery may enhance the efficacy of the active agent. This may in turn help prevent toxic side effects that are associated with the administration of high doses of various active agents or effects associated with the carrier itself (e.g. lipids, exogenous targeting moieties). In certain embodiments, it may be possible to treat or detect diseases with low doses of an active agent in a targeted manner without affecting uninvolved regions of the body.

The invention also contemplates hybridosome comprising BDMs with endogenously available targeting moieties that may facilitate successful delivery of active agents to cell types known in the art as being hard to transfect in vivo and in vitro (e.g. stem cells and immune cells). For example, hybridosomes comprising BDMs derived from leukocytes may show cellular enhanced uptake while EDEMs alone show reduced cellular uptake.

The hybridosome of the present invention may be used for treating, monitoring, preventing and/or diagnosing a number of diseases and conditions (e.g., inflammation, such as inflammation associated with cancer). Certain embodiments can involve delivery of the same or possibly different therapeutic agents to a site affected by a disease or condition. In some embodiments, the delivery systems of the present invention may be particularly useful for oncological applications, such as for the treatment, monitoring, prevention and/or diagnosis of a cancerous condition (e.g., malignant tumor cell). In such embodiments, the hybridosome of the present invention may be used for delivering an active agent (e.g., a therapeutic and/or a diagnostic agent) to a site affected with cancer (e.g., a tumor). Non-limiting examples of cancerous conditions that may be treated, monitored, prevented and/or diagnosed include, without limitation, leukemia, lymphoma, skin cancers (including melanomas, basal cell carcinomas, and squamous cell carcinomas), epithelial carcinomas of the head and neck, lung cancers (including squamous or epidermoid carcinoma, small cell carcinoma, adenocarcinoma, and large cell carcinoma), breast cancer, gastrointestinal tract cancers, malignant tumors of the thyroid, sarcomas of the bone and soft tissue, ovarian cancer, carcinoma of the fallopian tube, uterine cancer, cervical cancer, prostatic carcinoma, testicular cancer, bladder cancer, renal cell carcinoma, pancreatic cancer, and hepatocellular cancer. In some embodiments, the present invention provides a method for treating a subject with a cancer characterized by solid tumors. In some embodiments, the disease is selected from the group consisting of a cancer and Parkinson's disease.

In additional embodiments, the hybridosome of the present invention may be used to deliver an active agent to virus-infected cells. In such embodiments, the hybridosome of the present invention may be used for treating, monitoring, preventing and/or diagnosing viral infections.

In some embodiments, the hybridosome of the present invention may be used for targeting an inflamed site in a subject. Therefore, in such embodiments, the hybridosome of the present invention may be used for treating, preventing, monitoring and/or diagnosing a condition or disease associated with an inflammation. Representative conditions include, without limitation: allergies; asthma; Alzheimer's disease; diabetes; hormonal imbalances; autoimmune diseases, such as rheumatoid arthritis and psoriasis; osteoarthritis; osteoporosis; atherosclerosis, including coronary artery disease; vasculitis; chronic inflammatory conditions, such as obesity; ulcers, such as Marjolin's ulcer; respiratory inflammations caused by asbestos or cigarette smoke; foreskin inflammations; inflammations caused by viruses, such as Human papilloma virus, Hepatitis B or C or Epstein-Barr virus; Schistosomiasis; pelvic inflammatory disease; ovarian epithelia inflammation; Barrett's metaplasia; *H. pylori* gastritis; chronic pancreatitis; Chinese liver fluke infestation; chronic cholecystitis and inflammatory bowel disease; inflammation-associated cancers, such as prostate cancer, colon cancer, breast cancer; gastrointestinal tract cancers, such as gastric cancer, hepatocellular carcinoma, colorectal cancer, pancreatic cancer, gastric cancer, nasopharyngeal cancer, esophageal cancer, cholangiocarcinoma, gall bladder cancer and anogenital cancer; integumentary cancer, such as skin carcinoma; respiratory tract cancers, such as bronchial cancer and mesothelioma; genitourinary tract cancer, such as phimosis, penile carcinoma and bladder cancer; and reproductive system cancer, such as ovarian cancer. The hybridosome of the invention can be used in conjunction or concurrently with other known methods of disease treatment, including, but not limited to, chemotherapy and radiotherapy.

In one embodiment, the present invention provides a method of modulating the expression of a target polynucleotide or polypeptide. These methods generally comprise contacting a cell with a hybridosome of the present invention that is associated with a nucleic acid capable of modulating the expression of a target polynucleotide or polypeptide.

In related embodiments, the present invention provides a method of treating a disease or disorder characterized by overexpression of a polypeptide in a subject, comprising providing to the subject the hybridosome of the present invention, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

These methods may be carried out by contacting the hybridosome of the invention with the cells for a period of time sufficient for intracellular delivery to occur (e.g. inside the nucleus). Typical applications include using well known procedures to provide intracellular delivery of siRNA to knock down or silence specific cellular targets. Alternatively applications include delivery of DNA or mRNA sequences that code for therapeutically useful polypeptides. In this manner, therapy is provided for genetic diseases by supplying deficient or absent gene products.

Also contemplated by the present invention is the co-delivery of one or more unique encapsulated materials to target cells by the hybridosome described herein. Accordingly, by merging two unique EDEMs with unique active agents into a single hybridosome, a specific embodiment may be used to treat a single disorder or deficiency, wherein each such active agent functions by a different mechanism of action. For example, the hybridosome of the present invention may merge with both an EDEM comprising an encapsulated polynucleotide, intended to deactivate or "knockdown" a malfunctioning endogenous polynucleotide and its protein or enzyme product, and a second EDEM comprising an encapsulated enzyme, intended to provide enzyme replacement. In certain embodiments, an EDEM containing diagnostic agents, such as gold nanoparticles, can be fused with a BDM in a hybridosome treat a disorder and located affected cells or organs through diagnostic visualization techniques. Alternatively, specific embodiments of the present invention, may facilitate co-delivery of, for example, two unique endogenously produced polynucleotides (e.g., miRNA), by merging two unique BDMs into the identical EDEM.

In one embodiment of the present invention are suitable for the treatment of diseases or disorders relating to the deficiency of proteins and/or enzymes within or secreted by the target cell For example, the symptoms of a disease may be improved by providing the compositions of the invention (e.g. cystic fibrosis). Disorders for which the present invention are useful include, but are not limited to, disorders such as Pompe Disease, Gaucher Disease, beta-thalassemia, Huntington's Disease, Parkinson's Disease, muscular dystrophies (such as, e.g. Duchenne and Becker), hemophilia diseases, SMN1-related spinal muscular atrophy (SMA), amyotrophic lateral sclerosis (ALS), galactosemia, Cystic Fibrosis (CF), galactocerebrosidase deficiencies, Friedreich's ataxia, Pelizaeus-Merzbacher disease, and Niemann-Pick disease.

Additionally the invention provides a new platform for the development of highly immunogenic vaccines based on the co-delivery of a BDM capable of presenting an antigen and adjuvant containing EDEM. The combined delivery of adjuvants with antigen presenting BDMs represents a promising strategy for therapeutic vaccines to elicit an innate immune response by exploiting the major properties of the two components: (1) the strong adjuvanticity provided by the EDEM; and (2) the specific adaptive immune response against antigen(s) presented by the BDM and associated with the targeted disease. For example, the BDM may present any disease-associated antigen, such as one or more tumor associated antigen for cancer therapy, one or more pathogenic antigen for treatment of infection, or any other antigen or combination of antigens associated with other diseases, in particular for immune-compromised conditions and/or where strong potentiation of immunity is needed (e.g. in the elderly). In addition the invention provides hybridosome compositions which induce a strong immune response important for vaccines such as those against cancer, hepatitis, flu, malaria and HIV. The invention is also useful for any therapy where the presentation of a combination of antigens to the immune system of a patient may be beneficial.

In a further embodiment, an immune response may be elicited by delivering a hybridosome which may include a disease associated antigen. (U.S. Publication No. 20120189700; which is herein incorporated by reference in their entirety). In one embodiment, the EDEM may be formulated for use in a vaccine such as, but not limited to, against a pathogen or cancer.

In one embodiment, the EDEM may be formulated for use as a vaccine. In one embodiment, the EDEM may encapsulate at least one modified nucleic acid molecule and/or mRNA which encodes at least one antigen. As a non-limiting example, the EDEM may include at least one exogenous antigen and an excipient for a vaccine dosage form (see International Pub No. WO2011150264 and US Pub No. US20110293723, each of which is herein incorporated by reference in their entirety). The vaccine dosage form may be selected by methods described herein, known in the art and/or described in International Pub No. WO2011150258 and US Pub No. US20120027806, each of which is herein incorporated by reference in their entirety).

In one embodiment, the EDEM may comprise at least one adjuvant. In another embodiment, the EDEM may comprise at least one therapeutic agent and at least one adjuvant. As a non-limiting example, the EDEM comprising an adjuvant may be formulated by the methods described in International Pub No. WO2011150240 and US Pub No. US20110293700, each of which is herein incorporated by reference in its entirety.

In one embodiment, the EDEM may encapsulate at least one exogenous disease associated antigen which encodes a peptide, fragment or region from a virus. As a non-limiting example, the EDEM may include, but is not limited to, the antigens described in International Pub No. WO2012024621, WO201202629, WO2012024632 and US Pub No. US20120064110, US20120058153 and US20120058154, each of which is herein incorporated by reference in their entirety.

The hybridosome of the present invention may be used to deliver a therapeutic agent to a cell or tissue, in vitro or in vivo. The methods and formulations may be readily adapted for the delivery of any suitable therapeutic agent for the treatment of any disease or disorder that would be acceptable for such treatment. Methods of the present invention may be practiced in vitro, ex vivo, or in vivo. For example, the hybridosome of the present invention can also be used for delivery of nucleic acids to cells in vivo, using methods which are known to those of skill in the art. In a further aspect, the invention provides a pharmaceutical composition comprising a hybridosome of the invention and a pharmaceutically acceptable diluent. Examples of pharmaceutically acceptable diluents include solutions for intravenous injection (e.g., saline or dextrose). The composition can also take the form of a cream, ointment, gel, suspension, or emulsion.

For in vivo administration, the pharmaceutical compositions comprising the hybridosome of the invention are preferably administered parenterally (e.g., intraarticularly, intravenously, intraperitonealy, subcutaneously, or intramuscularly). In particular embodiments, the pharmaceutical compositions are administered intravenously or intraperitoneally by a bolus injection. Other routes of administration include topical (skin, eyes, mucus membranes), oral, pulmonary, intranasal, sublingual, rectal, and vaginal. Furthermore a pharmaceutical composition may be prepared, suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of any additional ingredients described herein.

In a further aspect, the invention provides a pharmaceutical composition according to the above for the delivery of diagnostic agents.

Beside the delivery of active agents for treatment, the hybridosome of the present invention may provide a mean for detection of tissue and cells affected by a disease or a condition, as well as detection of progression or relapse post therapy. Current non-invasive imaging relies on the use of contrast agents that take advantage of increased metabolic and amino acid metabolism within tumors, but these are limited by background noise and nonspecific uptake. Thus, the invention provides a pharmaceutical composition according to the above for the delivery of diagnostic agents directly to the target site, such as a tumor site and/or an inflammation site, to enable diagnostic imagining and precise localization thereof.

In a further aspect, the invention provides a process for manufacturing a hybrid biocompatible carrier (hybridosome) which comprises structural and bioactive elements originating from at least one biocompatible delivery module (BDM) and at least one engineered drug encapsulation module (EDEM) comprising at least one tunable fusogenic moiety, said process comprising:

(a) providing at least one EDEM having at least one fusogenic moiety or a composition comprising the same;
(b) providing at least one BDM or a composition comprising the same;
(c) contacting said at least one EDEM with said at least one BDM at a pH below 7.4 and at a temperature of between 0° C. and 60° C., thereby uniting said at least one EDEM with said at least one BDM and producing said hybridosome; and optionally
(d) purifying said hybridosome from non-fused EDEMs and/or BDMs.

The process of the invention has several important characteristics which make it of substantial utility to the art. The present invention provides a process for creating hybridosome by uniting one or more EDEMs and one or more BDMs to make a hybrid component displaying the characteristics of the original EDEM and BDM components. Uniting EDEMs with BDMs involves at least one fusogenic species present in any of the two components whose fusogenicity is tunable by changing the reaction environment. In certain embodiments the EDEMs (e.g., iLNPs) selectively exhibit an enhanced ability (e.g., electrostatic interaction) to unite with BDMs. In certain embodiments the BDMs (e.g., exosomes) selectively exhibit an enhanced ability (e.g., higher membrane fluidity) to unite with BDMs. Accordingly, provided herein, are processes for generating hybridosomes by defining the reaction environments. Such processes generally comprise the step of contacting BDMs with the EDEMs used herein (e.g., an iLNP) such that the contact causes simple aggregation and/or membrane disruption with lipid mixing via hemifusion and/or fusion, resulting in merging of some portion of the EDEM and BDM populations into a sub-population of hybridosomes. Hereby the contemplated processes have substantial advantages due to the means of inducing, controlling, restricting and/or terminating the respective uniting mechanism. Furthermore the process of the invention allows modular entities to be replaced or rearranged to make a therapeutically relevant architecture.

In one embodiment, an aqueous EDEM mixture comprising pre-formed vesicles with defined morphology and physical characteristics, wherein one or more lipids have or assume fusogenic characteristics, are added to a single chamber by one inlet and an aqueous mixture of collected BDMs is added into a second inlet. The components are then brought into contact in a common chamber. In one embodiment, said contact is enhanced by mixing the original compositions via diffusion. In a preferred embodiment mixing occurs by mechanical means (e.g. shaking). Alternatively, the uniting of BDMs and EDEMs may be facilitated via controlled fluid dynamics such as in a microfluidic mixing device. In such an embodiment, EDEMs and BDMs are injected into separate inlets of a microfluidic chamber and controlled mixing occurs via the chamber geometry and flow profile.

The invention relates to a process for producing hybridosome where said process provides control over fusogenic properties of EDEMs and BDMs. For the production of the hybridosome of this invention, inclusion of a reaction environment in which components of EDEMs and/or BDMs assume increased fusogenic attributes is a preferred embodiment. In one embodiment, acidic reaction environment increases net cationic surface charge of EDEMs and may simultaneously have BDMs assume increased net anionic surface charge. In preferred embodiment, uniting takes place in an acidic buffer with a pH between about 4 and about 6.

Without being bound to any theory, in another embodiment, reaction temperature may be modulated to cause a lipid phase transition in EDEMs from bilayer to hexagonal phase while simultaneously decreasing membrane rigidity in BDMs. The reaction temperature is limited to about 60° C. due to potential degradation of BDM constituents (e.g. proteins). In a preferred embodiment, a reaction temperature is set to 37° C. In one embodiment, the reaction environment displays physiological ionic strength. The present invention contemplates but is not limited to using mixtures of NaCl or KCl. In a further embodiment, the reaction solution may have calcium ions present.

The invention thus provides a process for producing hybridosome wherein uniting EDEMs and BDM is facilitated by co-incubation in a reactive environment over a period of time, including but not limited to 5 minutes, 15 minutes, 30 minutes, 1 hour, 2 hours, 5 hours or more. In one preferred embodiment, co-incubation takes place for about 1 hour.

In particular variations of this process, the mixing environment is altered to limit unification of the modules. In general, EDEM and BDM unification is controlled by a number of parameters, which may include particle concentration net surface charge, charge density, pH, ionic strength, additive concentrations and temperature. Methods for altering a mixing environment are well known in the art. For example, but not limited to, addition of solutions with higher buffering capacities or dialyzing module mixtures may be used to alter reaction solution properties. In one preferred embodiment, desalting columns can be employed to change solute properties.

The invention further relates to a process for producing hybridosomes where the process may optionally include the step of purifying these hybridosomes from excess individual modules. For the production of the hybridosomes of this invention, inclusion of the purification step is a preferred embodiment. Where purification of the hybridosomes is desired, purification may be accomplished by centrifugation through a sucrose density gradient or other media which is suitable to form a density gradient. However, it is understood that other methods of purification such as chromatography, filtration, phase partition, precipitation or absorption may also be utilized. Purification methods include, for example, purification via centrifugation through a sucrose density gradient, or purification through a size exclusion column. The sucrose gradient may range from about 0% sucrose to about 60% sucrose, preferably from about 5% sucrose to about 30% sucrose. The buffer in which the sucrose gradient is made can be any aqueous buffer suitable for storage of the fraction containing the complexes and preferably, a buffer suitable for administration of the hybridosomes to cells and tissues. Alternate separation techniques may include, but are not limited to, isoelectric focusing and/or immunoaffinity chromatography. For example, EDEMs comprising ionizable lipids display a net cationic surface charge and can be separated via electrophoresis. In one embodiment of the present invention, purification of hybridosomes may be achieved by sequential purification techniques. For example, a first immunoaffinity chromatography relating to affinity to BDM surface molecules followed by a second immunoaffinity chromatography relating to affinity of PEG molecules can sequentially separate hybridosomes from excess BDMs and EDEMs. A further separation technique could encompass asymmetric flow field flow fractionation coupled with multi angle light scattering to fractionate the reactant and product vesicles.

The EDEMs used in the method of the invention facilitate or enhance the encapsulation and release of encapsulated materials (e.g., an active agent) to one or more target BDMs (e.g., by permeating or fusing with the lipid membranes of BDMs). In certain embodiments, the structural characteristics of EDEMs and BDMs described herein demonstrate high fusion efficiencies. The term "fusion efficiency" refers to the relative amount of hybridosomes generated from EDEMs and BDMs which are subject to fusion. In certain embodiments, the structural characteristics of EDEMs and BDMs described herein demonstrate high fusion efficiencies thereby improving the likelihood that appropriate amounts of encapsulated materials (e.g., active agent) and endogenous biomaterial will be combined in a hybridosome and subsequently minimizing potential systemic adverse effects or toxicity associated with the compound or their encapsulated contents.

In certain embodiments, the EDEM formulations have tunable attributes to impart the production of the hybridosome of which such a module is a component (e.g. membrane compatibility). For example, the incorporation of ionizable lipids, helper lipids, PEG-modified lipids, pH-responsive polymers and/or pH activated cell penetrating peptides into the EDEM disclosed herein, may control the fusogenicity of such a module (or of the hybridosome of which such module is a component) with the lipid membrane of one or more target BDMs, thereby enhancing, for example, the control over EDEM-BDM unification. Without being bound by a specific theory, the relative molar ratio of iLNP lipids to each other is based upon the characteristics of the selected lipids, the nature of the target BDM, the characteristics of the materials encapsulated and those of the intended delivery target (e.g. cell, tissue or organ). Additional considerations include, for example, the toxicity, size, charge, pKa, fusogenicity and the saturation of the alkyl chain of the selected lipids.

In certain embodiments, the ionizable lipid content of EDEM compositions used herein are characterized as having one or more properties that afford such modules advantages relative to other classified subunits. For example, in certain embodiments, the EDEMs used herein allow for the control and tailoring of the uniting properties (e.g., surface charge). In particular, the compounds disclosed herein may be characterized by defined and tunable cationic nature as well as their ability to unite with potentially oppositely charged BDMs. Such abilities may include, for example controlled ion pair formation, fusogenicity capabilities and/or promoting the release of encapsulated materials (e.g., active agents) into the generated composition.

In certain embodiments, the EDEM formulations have tunable attributes to impart the membrane compatibility between EDEMs and BDMs. For example, the tailored incorporation of helper lipids into the EDEM disclosed herein, may allow for compatible membrane rigidity of such a module to facilitate uniting with the lipid membrane of one or more target BDMs. Specifically, the relative molar ratio of lipids and sterols such as cholesterol may be matched to be similar to the characteristics of the target BDM. Additional considerations include, for example, the resulting rigidity of the hybridosome of which such module is a component, to ensure interaction with the target cell or tissue.

In one embodiment of the present invention, BDMs have tunable attributes to impart the membrane compatibility between EDEMs and BDMs. For example a high content of BDM membrane components, such as but not limited to, sphingomyelin, saturated fatty acids incorporated into phospholipids and cholesterol may account for a higher rigidity than the donor cell it was derived from. Simultaneously, as the BDM membrane components may be different from the plasma membrane of the cells from which a BDM is derived, leading to a higher rigidity, BDMs may show enhanced stability during the manufacture process. However, in an acidic pH environment (e.g. about pH 5), the BDM membrane of the present invention is contemplated to display lower rigidity (and higher fusogenicity) and may allow for uniting with the membrane of EDEM.

In certain embodiments, the incorporation of ionizable lipids, for example, with one or more alkyl amino groups or moieties into the used EDEMs (e.g., as a head-group) may further promote disruption of the BDM membrane by exploiting their fusogenicity. This may be based not only on the optimized pKa and therefore the pH dependent cationic nature the lipid, but also the optimized phase transition temperature, promoting a transition from a bilayer phase to the highly fusogenic reverse hexagonal $H_{II}$ phase (Semple et al., 2010). The result is believed to promote formation of ion pairs between ionizable lipids in their cationic state and anionic lipids, hereby disrupting the BDM membrane structure and transferring the contents into the hybridosome.

The EDEMs used herein may be used to produce pharmaceutical compositions that facilitate or enhance the encapsulation and release of encapsulated materials (e.g., active agents) to one or more target BDMs (e.g., by permeating or fusing with the lipid membranes of BDMs). For example, when a lipid-based composition (e.g., a iLNP) comprises or is otherwise enriched with one or more of the ionizable lipids, the phase transition in the lipid bilayer of the one or more BDMs may facilitate the delivery of the encapsulated materials (e.g., active agents encapsulated in a lipid nanoparticle) into one or more hybridosomes.

In certain embodiments of this invention, the control over the total amount of ionizable lipids within EDEMs may serve to control structural characteristics of hybridosomes disclosed herein. Accordingly, in certain embodiments of the present invention, the physical characteristics of the EDEMs are proportional to the ionizable lipid content. For example, EDEMs with small diameter may have a lower overall ionizable lipid content compared to EDEMs with larger diameter. Consequently, one or more of the EDEMs disclosed herein may unite with the identical BDM until a neutral net-surface charge and a hereby limited dimension is achieved.

In one embodiment of this invention, EDEMs can be manufactured to encapsulate enzymatic and bioactive catalytic compounds that upon integration into the hybridosome are capable of interacting with one or more compounds originating from the BDM. For example, EDEMs can be manufactured to contain ribonucleases, capable of degradation of any endogenous polynucleotides transferred into a hybridosome by the BDM.

The following examples, which further describe the invention, are offered by way of illustration and are not intended to limit the invention in any manner.

Example 1

Production of iLNPs as Engineering and Drug Encapsulating Modules

Materials and Methods for Examples 1-4
A) Chemicals
1,2-distearoyl-sn-glycero-3-phosphoethanolamine-N-[amino(polyethylene-glycol)-2000] (amine-PEG-DSPE), [1,2-dioleoyl-sn-glycero-3-phosphoethanolamine-N-(7-nitro-2-1,3-benzoxadiazol-4-yl)] (NBD-PE), 1,2-distearoyl-sn-glycero-3-phosphoethanolamine-N-[maleimide (polyethylene glycol)-2000] (mal-PEG-DSPE), Distearoyl-phosphatidylcholine (DSPC), 1,2-dioleoyl-3-dimethylammonium-propane (DODAP), N-palmitoyl-sphingosine-1-succinyl[methoxy(polyethylene glycol)2000] (PEG-Cer) and cholesterol were purchased from Avanti Polar Lipids (Alabaster, Ala.). The syntheses of 1,2-dilinoleyloxy-3-dimethylaminopropane (DLinDMA) and PEG-lipids have been described previously (Heyes, Palmer, Bremner, & MacLachlan, 2005).

B) Extrusion-Based Formulation of iLNPs
Preparation of Preformed Vesicles:
Depending on desired properties of the vesicle, the ionizable cationic lipid (DLinDMA or DODAP), DSPC, cholesterol and PEG-lipid (PEG-s-DMG or PEG-Cer) were solubilized in ethanol at an appropriate molar ratio (e.g. 40:17.5:40:2.5). To form vesicles, the lipid formulation was mixed into a low pH aqueous buffer (50 mM acetate, pH 4) under vortexing until reaching a final concentration of approximately 10 mM and a 3:7 ethanol-to-aqueous ratio. The generated multi-laminar vesicles were then extruded through two stacked 80 nm or 100 nm pore-sized Nuclepore™ polycarbonate filters (Whatman) using a Mini-Extruder (Avanti,) at room temperature.

Preformed Vesicle Oligonucleotide Encapsulation:
The oligonucleotide encapsulation was achieved using the previously described preformed vesicle method (Maurer et al., 2001). In general, the oligonucleotide was solubilized in an aqueous solution matching that of the extruded vesicles (50 mM acetate, pH 4, 30% ethanol) and subsequent drop wise adding to the unilamellar vesicles under vortex mixing. The plasmid, siRNA and shRNA encapsulation was performed at a 1:30 plasmid-to-lipid wt/wt ratio and 1:16 RNA-to-lipid wt/wt ratio, respectively. The mixture was then incubated at 37° C. for 30 min followed by removal of residual ethanol and buffer exchange via extensive dialysis against PBS (pH 7.4) at 4° C. Unencapsulated shRNA and plasmid were removed via an anion exchange spin column (Pierce—Thermo Fisher Scientific Inc.), equilibrated to PBS (pH 7.4). Efficiency of oligonucleotide encapsulation was determined by 260 nm absorption (Spectramax M5e, Molecular Devices) after solubilizing the loaded vesicles in a 1:5 volume ratio with acidic-isopropanol (10% HCl).

Protein Encapsulating iLNPs:
In comparison to the protocol above, iLNPs encapsulating Bovine Serum Albumim (BSA, Sigma Aldrich) and human Hemoglobin (Sigma Aldrich) were made by dissolving the protein into the aqueous buffer (50 mM sodium acetate, pH 5.5) beforehand to reach a final concentration of 1.5 mg/ml and 1 mg/ml, respectively, followed by the drop wise addition of the ethanolic solution (20% final EtOH content) of the lipid mix (40:17.5:40:2.5 molar ratio of DlinDMA:DSPC:Chol:PEG-Cer) under vortex mixing. This solution was incubated at 37° C. for 1 h. Lipid vesicles encapsulating BSA were extruded as described above. Removal of free protein, residual ethanol and buffer exchange was achieved via extensive dialysis (300 kDA MWCO, Spectrumlabs) against PBS (pH 7.4, 4° C.). Protein encapsulation efficiency was determined via a BCA™ Protein Assay Kit (Pierce—Thermo Fisher Scientific Inc.,) after solubilizing the iLNP with 10% Triton X-100 (Sigma Aldrich). Extensive removal of free protein was monitored by withholding the detergent during protein quantification.

Small Molecule Encapsulating iLNPs:
Similar to the protocol above, iLNPs encapsulating carboxyfluorescein were made by dissolving the small molecule into the aqueous buffer (25 mM sodium acetate, pH 5.5) beforehand to reach a final concentration of 1 mM, followed by the drop wise addition of the ethanoic solution (20% final EtOH content) of the lipid mix (40:17.5:40:2.5 molar ratio of DODAP:DSPC:Chol:PEG-Cer) under vortex mixing. This solution was incubated at 37° C. for 1 h followed by extrusion as described above. Removal of small molecules, residual ethanol and buffer exchange was achieved via extensive dialysis (300 kDA MWCO, Spectrumlabs) against PBS (pH 7.4, 4° C.).

Figure 2:
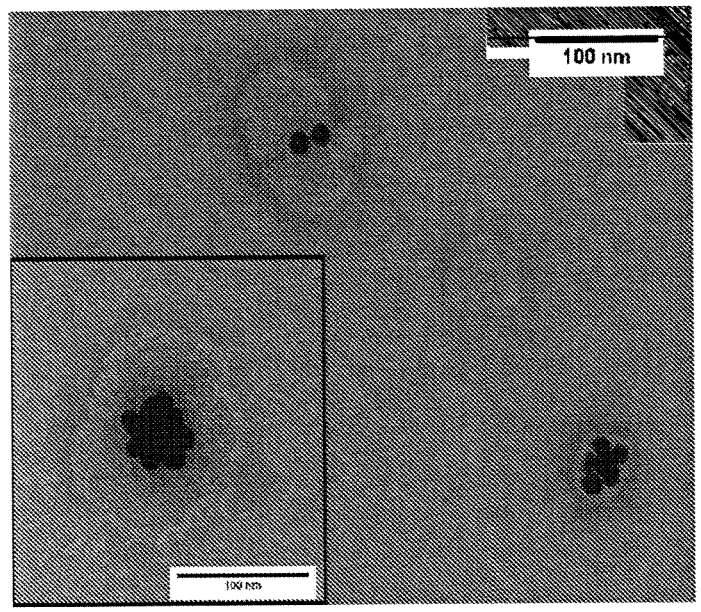
FIG. 2 is a transmission electron microscopy (TEM) picture of Au-iLNPs (scale bar: 100 nm)

Au-Nanoparticle Encapsulating iLNPs:

Due to the instability of Au nanoparticles in ionic buffer, encapsulation of 20 nm Au Nanoparticles (Nanocs Inc.) was achieved by keeping the Au Nanoparticles in deionized water solution at a gold-to-lipid weight ratio of 1:20. As described above, the ethanolic lipid mixture was added, the solution extruded and buffer exchanged to PBS via dialysis. In PBS, free Au nanoparticles aggregate and sediment. The presence of encapsulated gold nanoparticles was monitored by UV-Vis absorbance of Au-iLNPs around the plasmon resonance wavelength of 525 nm as well as Transmission Electron Microscopy (TEM). The increase in 450 nm UV-Vis absorption compared to empty vesicles was used to determine gold concentrations as previously described (Haiss, Thanh, Aveyard, & Fernig, 2007). As shown in FIG. 1, UV-Vis absorption spectra of both stock gold nanoparticles and Au-iLNPs show the characteristic surface plasmon resonance peak at approx. 550 nm. In detail, an encapsulation efficiency of 30% for Au-iLNPs and 26% for Au-DNA iLNPs was determined from the relative increase in 450 nm absorption reading compared to empty iLNPs and DNA-iLNPs. Electron micrographs shown in FIG. 2 supported the presence of encapsulated gold nanoparticles.

C) Microfluidic Based Formulation of iLNPs

Preparation of siRNA-Loaded Lipid Nanoparticles by Employing a Rapid Mixing Microfluidic System:

Lipid nanoparticles were prepared on a Nanoassemblr™ microfluidic system (Precision NanoSystems) according to the manufacturer's instructions. Depending on the desired formulation, an ethanol solution similar to that of the preformed vesicle approach, consisting of DLinDMA, cholesterol, DSPC and PEG-lipid at the appropriate molar ratio (e.g. 40:40:18:2), was prepared at concentrations of 10 mM total lipid. Furthermore an aqueous siRNA solution with a 1:16 siRNA to lipid wt/wt ratio was prepared in 25 mM acetate buffer at pH 4.0. Depending on the total volume of production 1 and 3 ml syringes where used to create the inlet stream with a total flow rate of 12 ml/min. For each formulation the aqueous siRNA solution was mixed with the ethanol-lipid solution with a flow rate ratio of 3:1 (Aq:Et) at room temperature. The product was then dialyzed against PBS to remove the residual ethanol as well as to raise the pH to 7.4 and free siRNA was removed as described with the preformed vesicle method above.

Example 2

Extracellular Vesicle (EV) Isolation as Biocompatible Delivery Modules

Exosomes:

Exosomes were isolated from the supernatant of mantle cell lymphoma (MCL-exo) and glioblastoma cell lines (GBM-exo) by differential centrifugations as previously described by Thery et al. (Théry, Amigorena, Raposo, & Clayton, 2006). Exosomes where then measured for their protein content using a BCA™ Protein Assay Kit (Pierce—Thermo Fisher Scientific Inc.) and exosome aliquots were stored at −80° C. For the additional purification, the exosome pellet was dissolved in PBS, layered on top of a sucrose cushion using standard protocols.

Microvesicles:

Human platelet- and activated polymorphonuclear neutrophil-derived microvesicles (PLT-MVs and PMN-MVs) samples were isolated from human specimens. In short, PLT-MVs were isolated by differential centrifugation of platelet concentrates derived from healthy donor blood transfusions as described before (Sadallah, Eken, Martin, & Schifferli, 2011). PMN-MVs were purified as recently published (Eken, Sadallah, Martin, Treves, & Schifferli, 2013); PMNs were isolated from a healthy blood donor fresh buffy coat. They were activated with formyl-methionyl-leucyl-phenylalanine and shed microvesicles were isolated via differential centrifugation.

Example 3

Surface Modification of iLNPs by Coupling Pegylated Lipids with Fab' Fragments, Antibody Fragments, Peptides and Glycosaminoglycans The engineering compatibility of iLNPs was demonstrated by conjugation of a reduced antibody, Fab' fragment, fusion peptide and glycosaminoglycan to a pegylated lipid anchored into the membrane of iLNPs. Compared to the formulation of example 1, 0.5 mol % of the pegylated lipid was substituted for PEG-modified lipids with a maleimide group or amine group at the distal end of the PEG. Conjugation was performed according to standard protocols based on reactions between; (1) maleimide groups at the distal PEG termini and free thiol groups of the reduced antibody, Fab' fragment or terminally thiolated peptides. (2) amine groups at the distal PEG termini and the activated carboxyl groups on the glycosaminoglycan chain of the glycosaminoglycan (GAG).

Methods:

Fab' Fragment:

First, Anti-CD38 F(ab)$_2$ fragments were reduced with 2-Mercaptoethylamine (MEA) (Pierce—Thermo Fisher Scientific Inc.) using a fifth of the final concentration mentioned by the supplier's instructions. 60 µg F(ab)$_2$ was incubated with 10 mM MEA in reaction buffer (1 mM EDTA, PBS) for 90 min at 37° C. MEA was removed by buffer exchange to reaction buffer with a Zeba™ Spin desalting column (Pierce—Thermo Fisher Scientific Inc.). iLNPs loaded with siRNA were immediately added (2:1 ratio mal:Fab') and incubated on a shaking plate at 4° C. overnight. Unbound antibodies/fragments were separated on a Sepharose CL-4B column equilibrated with PBS (pH 7.4). Fractions containing Fab' fragments were determined from absorbance reading at 280 nm, pooled together and concentrated in 10 kDa centrifugal filter (Amicon® Ultra-0.5, Merck Millipore). A gel electrophoresis (SDS-PAGE) under non-reducing conditions, using 10% acrylamide, was conducted to verify the integrity of the Fab' fragments following the F(ab)$_2$ to Fab' reducing process.

IgG Antibody:

IgG Antibodies were reduced with Dithiothreitol (DTT) (Sigma). Before the coupling reaction, the antibody was reduced with 25 mM DTT for 1 h at 4° C. in PBS. The reduced Ab was separated from excess DTT by use of a 40 kDa Zeba™ Spin desalting column (Pierce—Thermo Fisher Scientific Inc.) equilibrated with PBS (pH 7.4). The conjugation (1:4 ratio mal:antibody) was performed in PBS (pH 7.4) over night at 4° C. Unbound antibodies were removed on a Sepharose CL-2 column. Antibody conjugation was determined from absorbance reading at 280 nm, as described for Fab' fragments.

Peptide:

A 26-amino acid melittin analogue peptide with an N-terminal cysteine was conjugated to pDNA-iLNPs by mixing with the thiolated peptide at a 1:1 peptide-to-maleimide molar ratio and incubated overnight at room temperature.

Glycosaminoglycans:

Glycosaminoglycans (5 k MW) were conjugated to the amine group of the distal PEG termini via conventional EDC-Sulfo NHS coupling reaction. First the glycosaminoglycans were activated by EDC/NHS (1:1 ratio EDC:COOH, 1:1 ratio EDC/NHS) in DIW for 1 h followed by addition of iLNPs (5:1 ratio glycosaminoglycan:amine) in PBS (pH 8.2). The reaction was continued for 2 h and followed by dialysis against PBS (pH 7.4) at room temperature with a 10 kDa cutoff to remove the unbound glycosaminoglycans.

Successful conjugation was further determined by DLS measurement of the hydrodynamic diameter. As one can see in Table 1, comparison of the hydrodynamic diameter (Dh) by DLS, the mean diameter of iLNPs increased after coupling of IgGs, fusion peptides, Fab' fragments and glycosaminoglycans.

Example 4

Characterization of iLNPs and EVs Secreted In Vivo

Figure 3:
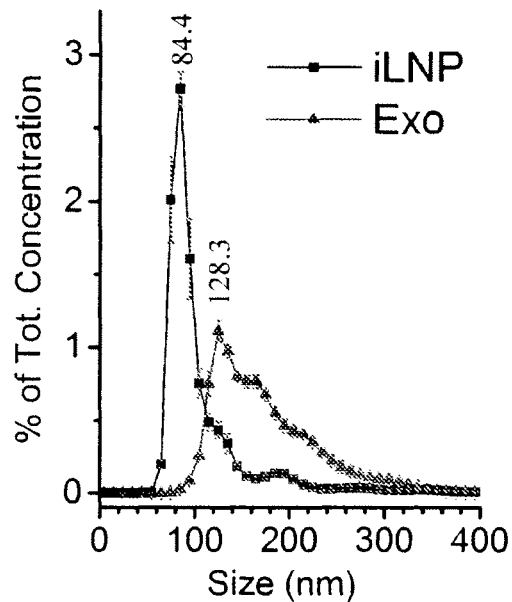
FIG. 3 is a histogram of GBM-exos and empty iLNPs diameters (obtained by nanoparticle tracking analysis (NTA)

After manufacture of iLNPs and isolation of EVs as described in examples 1, 2 and 3, size distributions of iLNPs and EVs were recorded using DLS (Zetasizer NS, Malvern) and NTA (LM20, Nanosight) using standard protocols. As shown in Table 1, average sizes increased with the encapsulation of cargo or surface modification of iLNPs. Due to the controlled synthesis conditions, iLNPs can be created with a small polydispersity index (PDI), which is also reflected in the sharp mono-modal NTA size distribution. As secreted vesicles, exosomes have an inherit polydispersity. As shown in FIG. 3, the single particle approach of the NTA analysis reveals a mono-modal size distribution for empty iLNPs and differently sized sub-populations of GBM-exo.

TABLE 1

Size determination of iLNPs and exosomes as well as cargo encapsulation efficiency

| Samples | DLS[a] $D_h$ (nm) | PDI | NTA[b] D (nm) | Standard Error | Cargo Encapsulation |
|---|---|---|---|---|---|
| Empty iLNPs | | | | | |
| 2.5% PEG | 66.8 | 0.167 | 84.4 ± 1.6 | 65.5 ± 1.9 | — |
| 10% PEG | 70.4 | 0.058 | — | — | — |
| DODAP ionized lipid | 121.2 | 0.098 | — | — | — |
| Oligonucleotide iLNPs | | | | | |
| GFP pDNA | 89.3 | 0.210 | 99.0 ± 4.1 | 85.0 ± 4.9 | 60.4%[c] |
| shRNA | 71.6 | 0.074 | 80.2 ± 0.8 | 30.0 ± 2.0 | 86.9%[c] |
| siRNA | 128.0 | 0.056 | — | — | 66.3%[c] |
| siRNA (microfluidic device) | 83.0 | 0.270 | — | — | 93.0%[c] |
| Surface Modified iLNPs | | | | | |
| 0.5% PEG-Mal (Empty) | 81.2 | 0.213 | — | — | — |
| 0.5% PEG-Mal (pDNA) | 108.4 | 0.194 | — | — | 63.8%[c] |
| 0.5% PEG-Mal (siRNA) | 111.0 | 0.049 | — | — | 83.43%[c] |
| 0.5% PEG-NH$_3$ (siRNA) | 129.1 | 0.088 | — | — | 77.8%[c] |
| IgG-Mal Conj. (Empty) | 108.2 | 0.281 | — | — | — |
| Pep.-Mal Conj. (pDNA) | 116.6 | 0.345 | — | — | — |
| Fab'-Mal Conj. (siRNA) | 126.4 | 0.052 | — | — | — |
| GAG-NH$_3$ Conj. (siRNA) | 189.3 | 0.248 | — | — | — |
| Protein iLNPs | | | | | |
| Bovine Serum Albumin | 155.9 | 0.210 | — | — | 0.599 mg/ml[e] |
| Hemoglobin | 202.5 | 0.274 | — | — | 0.080 mg/ml[e] |
| Nanoparticle iLNPs | | | | | |
| 20 nm Gold NP | 104.2 | 0.083 | — | — | 6.98 × 10$^{11}$ N/ml[f] |
| 20 nm Gold NP + pDNA | 96.1 | 0.155 | — | — | 6.06 × 10$^{11}$ N/ml[f] |
| Small Molecules | | | | | |
| Carboxyfluorescein | 83.6 | 0.106 | — | — | — |
| Exosomes | | | | | |
| GBM Exosomes | 127.7 | 0.250 | 128.3 ± 4.7 | 59.6 ± 4.8 | — |
| B-Cell Exosomes | 126.0 | 0.100 | 186[g] | 69[g] | — |

[a]Results represent mean of 3 experiments
[b]Results represnt mean ± SE of three 1800 frames
[c]A260 UV-Vis (post HCl—iPrOH disruption)
[d]A280 UV-Vis derived from unconjugated fractions
[e]BCA Protein Assay (post detergent disruption)
[f]A450 UV-Vis (gold only)
[g]Results represent 900 frames

Example 5

Controlled Initiation of the Interaction of BDMs and EDEMs

Figure 4:
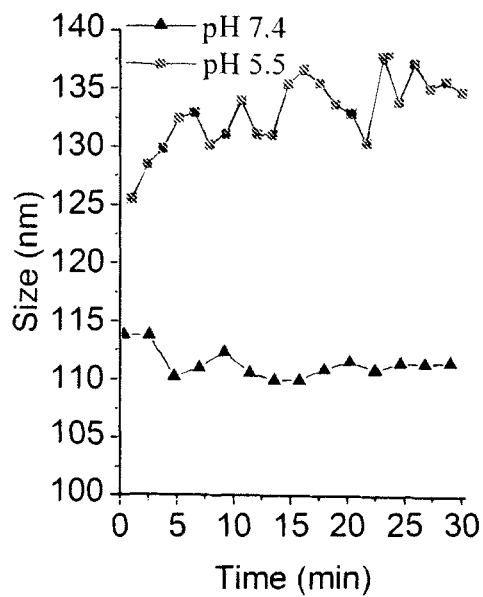
FIG. 4 is a graph showing the mean particle size after mixing GBM-exos and iLNPs under non-ionizing conditions (pH 7.4), or in fusion buffer (pH 5.5) (obtained via dynamic light scattering (DLS))

It was investigated whether the interaction between iLNPs and exosomes can be induced by changing the pH of the environment. As shown in FIG. 4, the mean diameter of an iLNP/exosome solution increases in the fusion (10 mM MES, pH 5.5, 145 mM NaCl, 5 mM KCl) buffer while no significant change is evident in a pH 7.4. As the ensemble nature of DLS measurements makes it difficult to positively deduce the presence of interactions between the two sub-units, the focus was next turned to the interaction between the lipid membranes of both exosomes and iLNPs.

Aside from size changes, lipid mixing between two membranes presents a further method to determine a fusion event. During a fusion process, the lipids from two membranes disperse within the newly formed membrane. Lipid mixing was monitored by the increase in fluorescence resulting from dilution of lipophilic self-quenching rhodamine dye (R18). Exosomes (20 µg of protein) were labeled with 1 µl of an ethanolic solution of octadecyl rhodamine B chloride (R18) (Biotium) (1 mM) in MES buffer (10 mM MES, pH 5.5, 145 mM NaCl, 5 mM KCl). This solution was incubated for 30 min at room temperature. The unincorporated R18 was removed by using a Zebaspin© desalting column (40 kDa cut off), equilibrated with a MES fusion buffer (10 mM MES, pH 5.5, 145 mM NaCl, 5 mM KCl). R18-labeled exosomes (5 µg of total protein) were suspended in the appropiate buffer in a stirred quartz-cuvette and sample fluorescence was measured via a LS55 spectrofluorometer (Perkin Elmer) at 560-nm excitation and 590-nm emission wavelengths. Following an equilibration time of 3 min, unlabeled iLNPs (30 µg total lipid) were added to the exosomes, and fluorescence was monitored for a further 30 min. Maximal R18 dilution was obtained by adding Triton X-100 to disrupt the membranes. The extent of lipid mixing was measured as the difference of equilibrated fluorescence from exosomes alone and expressed as % of maximal fluorescence de-quenching following detergent disruption. Analogous to exosomes, microvesicle samples (0.25 µg PLT-MVs and 1.2 µg PMN-MVs total protein) were labeled with ethanolic solution of R18, followed by free dye removal and monitoring of increase in fluorescence as mentioned above.

Figure 5:
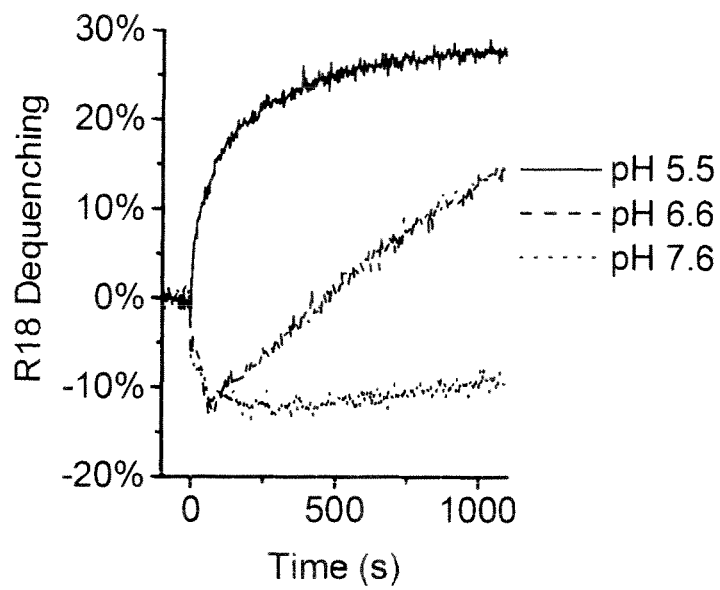
FIG. 5 is a graph showing the results of a R18 fusion assay of GBM-exos and iLNPs with varying buffer pH conditions.
Figure 6:
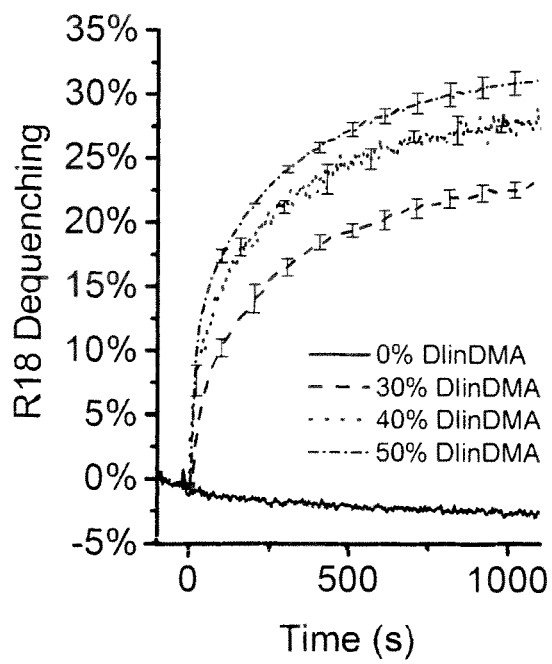
FIG. 6 is a graph showing the results of a R18 fusion assay of GBM-exos and iLNPs containing 0, 30, 40 or 50% DLinDMA content.
Figure 7:
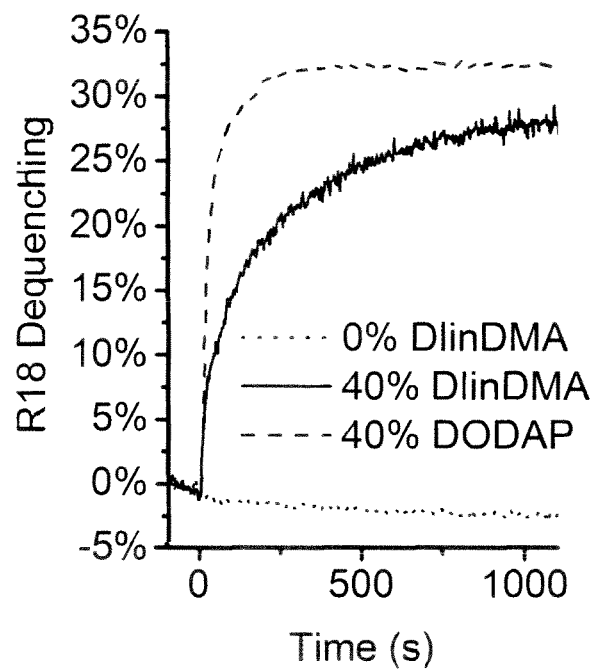
FIG. 7 is a graph showing the results of a R18 fusion assay of GBM-exo and iLNPs containing the ionizable lipid DODAP or DLinDMA.
Figure 8:
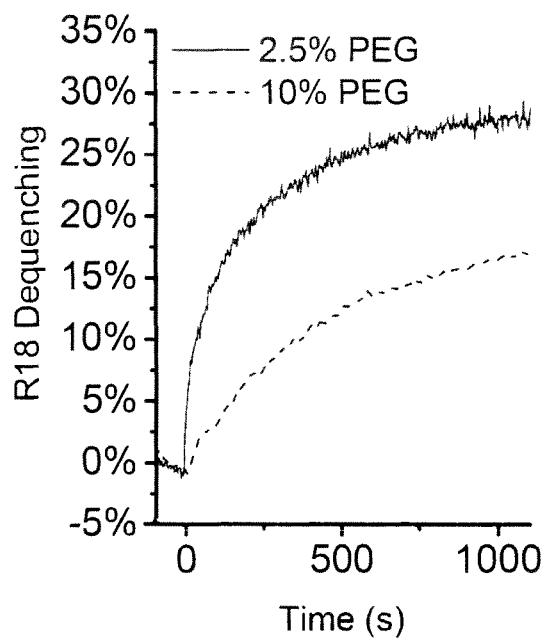
FIG. 8 is a graph showing the results of a R18 fusion assay of GBM-exos and iLNPs containing varying PEG-lipid content.
Figure 9:
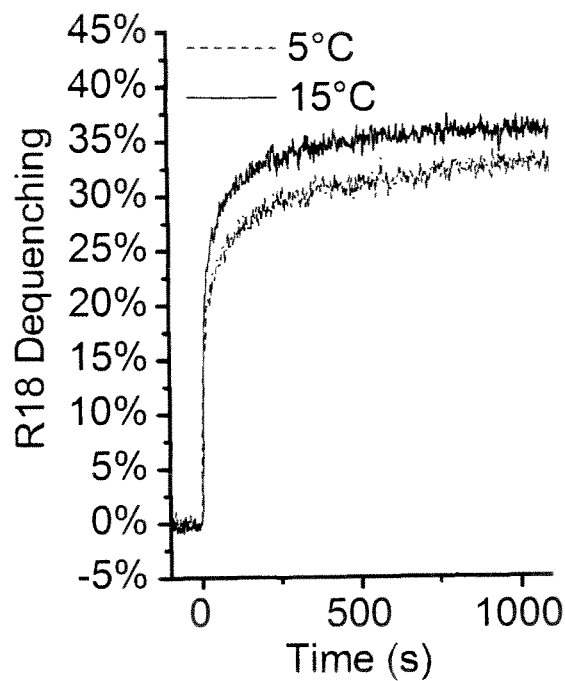
FIG. 9 is a graph showing the results of a R18 fusion assay of GBM-exos and iLNPs at varying temperatures.

Upon fusion between unlabeled iLNPs and R18 labeled exosomes, the rhodamine incorporated into the membrane of the exosome disperses into the unlabeled liposomal membrane portions, resulting in reduced close-quarter self-quenching and subsequently the fluorescence increases proportionally to the degree of membrane fusion. As shown in FIG. 5, rapid increase in fluoresence occurred at pH of 5.5, slower and continuous increase in fluoresence at a pH of 6.6, while lipid mixing was hampered at pH 7.6. To verify that the cationic nature of iLNPs was the driving force behind lipid mixing and not a change of pH, FIG. 6 shows that the addition of 0% DLinDMA liposomes (DSPC/Chol/PEG) resulted in no de-quenching. In order to rule out a fusogenic property specific to the ionizable lipid DLinDMA to potentially be the driving force behind lipid mixing, iLNPs were manufactured in which the DLinDMA was substituted by the ionizable lipid DODAP. Lipid mixing was observed upon adding these DODAP-iLNPs to R18 labeled exosomes (FIG. 7). Additionally, similar experiments were conducted when increasing the PEG-lipid content of iLNPs from 2.5 mol % to 10 mol % (FIG. 8) and varying the temperature (FIG. 9).

Example 6

BMD and EDEM Interaction Probed on Single Particles

Figure 10:
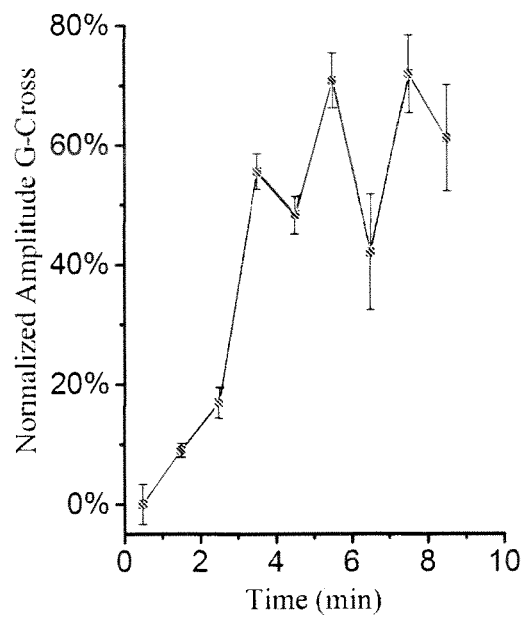
FIG. 10 is a graph obtained via fluorescence cross-correlation spectroscopy (FCCS) of a mixture of GBM-exos and iLNPs at pH 5.5.

The investigation next focused on the interaction between exosomes and iLNPs at the level of single particles. The temporal emergence of particles that comprised a mixture of exosomal protein and liposomal membranes was quantified in a fluorescence cross-correlation spectroscopy (FCCS) setup. In preparation for FCCS measurements, iLNPs membranes were labeled with lipophilic Bodipy™ (630/650) while exosomal surface proteins were labeled by conjugation with Bodipy™ NHS Ester (493/502). Both exosomes and iLNPs were then mixed in fusion buffer at comparable particle numbers and the emergence of correlated intensity fluctuations in both channels was recorded. Synchronized signals on both detectors represent either aggregated or fused exosomes and iLNPs, while individual particles generate temporally independent signals. In FIG. 10, the increase in the degree of cross-correlation (θ) when exosomes-Bodipy™ (493) and iLNP-Bodipy™ (630) were mixed, is shown over time. No correlation between the green and red channel was observed just after mixing of the two particles. Over the time course of 8 min the degree of cross correlation of the individual particles increased from 0% to approximately 70%, implying that nearly 70% of the total fluorescent bursts of probed particles exhibited exosomal surface proteins and liposomal membrane.

The detection minimum degree of cross-correlation was determined using a control mixture of two hydrophilic dyes (488 and 633). As positive controls, doubly labeled complementary DNA strands (488/633) IBA standards (IBA GmbH), were used to obtain the maximum achievable degree of cross-correlation.

Example 7

Fusogenic EDEMs and BDMs Fuse to Form Hybridosomes

Figure 11:
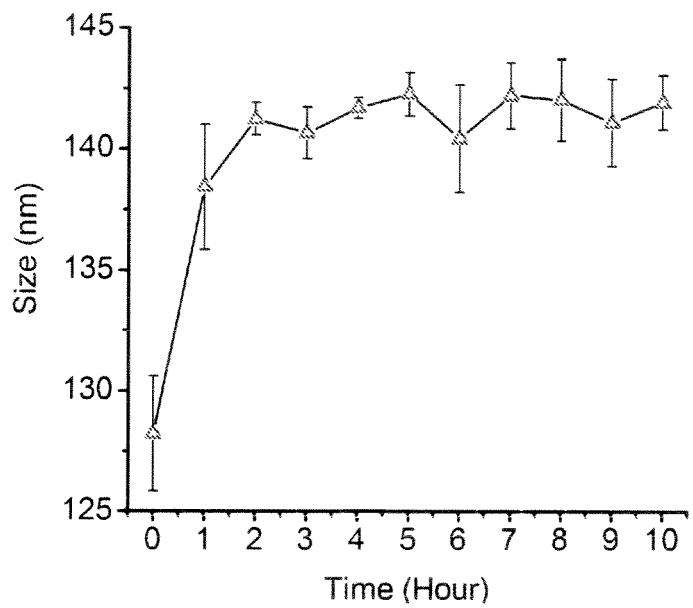
FIG. 11 is a graph showing the time-dependent change of the mean particle diameter of a mixture of GBM-exos and iLNPs at pH 5.5 monitored by dynamic light scattering (DLS)

In order to rule out the possibility of simple aggregation, structural rupture or false positive fusion assays due to lipid exchange, the mean size and size distribution of a cargo-less iLNP/exosome mixture in a pH 5.5 buffer was recorded at different time points via DLS and NTA. The same experimental conditions were used to monitor the z-average mean size for a period of 10 h. As shown in FIG. 11, within the first hour of mixing, the mean particle size rapidly increases and remains virtually unaffected over the next nine hours. In the case of aggregation, oppositely charged vesicles have the ability to continuously aggregate into electrostatically structured formations, yet this is not the case. A further indicator ruling out aggregation is the extent of diameter increase. The volume of two fused spheres scales with the radius in a $V \propto r^3$ fashion, whereby the fusion of a 85 nm and a 130 nm sphere would give rise to a 141 nm particle. In aggregation on the other hand, the radius scales linearly with every further sphere joining an aggregate. This would be evident by a large diameter increase in the range of multiples of the subunit diameter. This is further supported as shown in FIG. 12, a mixture of siRNA-iLNPs and MCL-exos in fusion buffer (stored at room temperature) showed no significant increase in mean diameter over the period of 9 days.

To rule out that the change in mean size or Gaussian size distribution revealed by DLS is not an artefact of averaging subpopulations, size distribution of exosomes, iLNPs and fusion products based on NTA-measurements of individual particles was evaluated. Prior to analysis, iLNPs and exosomes were diluted in fusion buffer (20'000-fold for iLNPs and 0.01 mg exosomal protein per ml). For the fusion reaction, exosomes and iLNPs were incubated at a 1:1 ratio and a sample taken from the reaction mix was recorded every 2 min. Per measurement a movie of 1800 frames was recorded. Data was analyzed using NTA Analytical Software suite version 3.0 with an auto setting of blur, minimum track length and minimum expected particle size.

Figure 13:
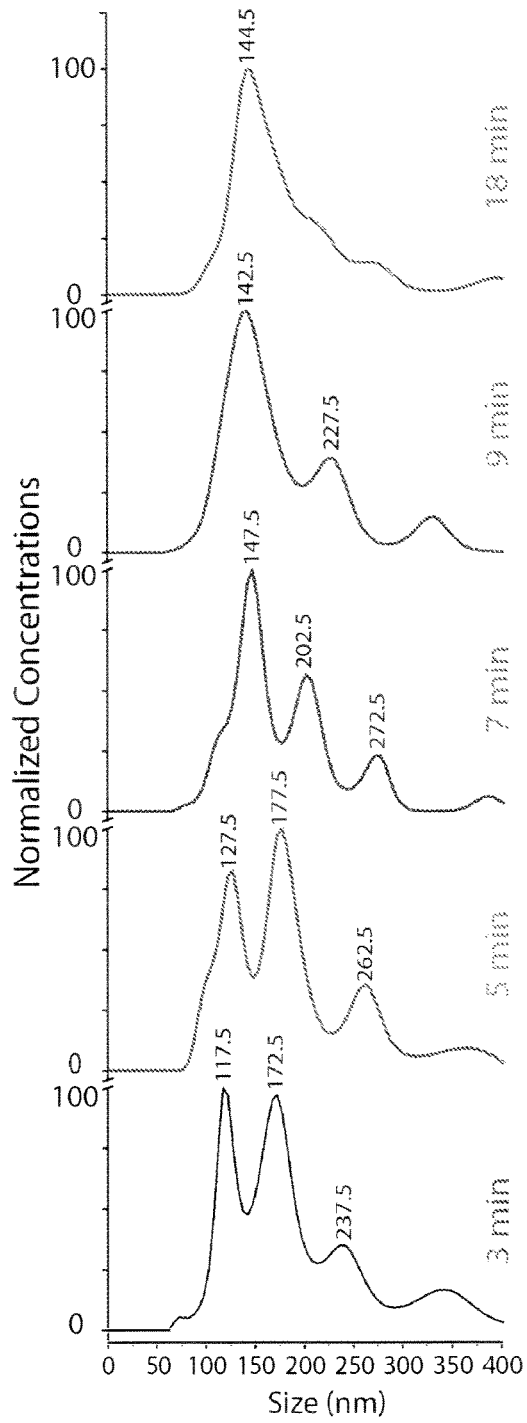
FIG. 13 displays five histograms showing the particle distributions of iLNPs and exosomes mixtures after 3, 5, 7, 9 and 18 minutes of mixing in pH 5.5.
Figure 14:
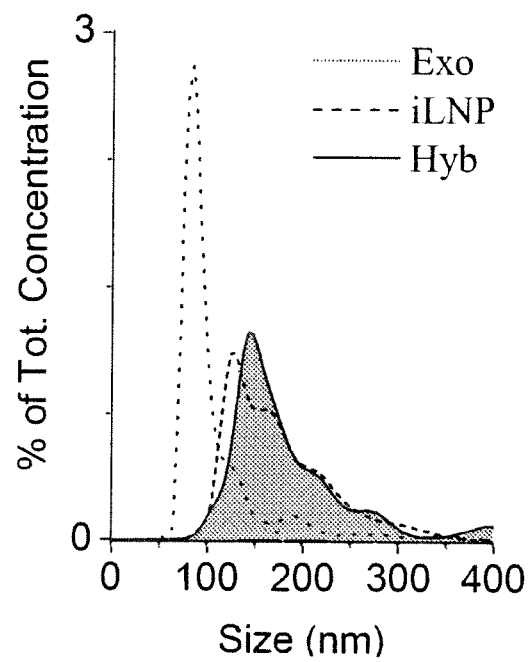
FIG. 14 is a graph showing the overlay of NTA size distributions of iLNPs, exosomes and hybridosomes.

Monitoring the size distribution in fusion reactions over time (FIG. 13) showed that after 3 min of mixing a 50-90 nm population of iLNPs is largely diminished and a subpopulation at 90-125 nm increases. Over the time course of 18 min, size distribution shows a peak of 144.2 nm particles and it may be deduced that by increasing the fusogenicity of EDEMs in the presence of BMDs gives rise to particles that display a distinct size distribution. These unique size profiles of exosomes, iLNPs and newly formed particles are depicted in FIG. 14. The population of newly formed vesicles is dubbed "hybridosomes".

Figure 12:
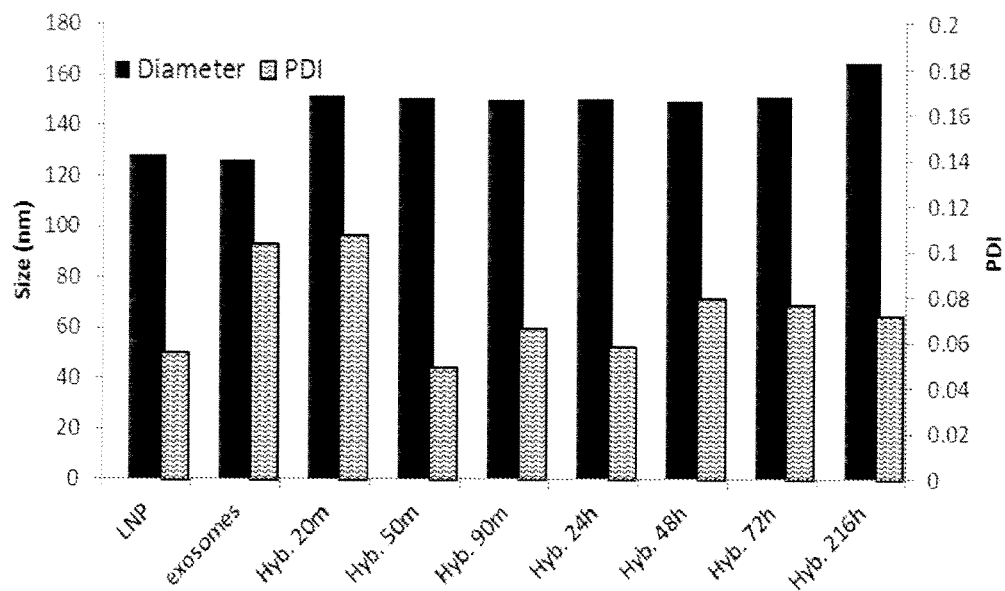
FIG. 12 is a graph showing the time-dependent change of the mean particle diameter and polydispersity index of a mixture of MCL-exos and iLNPs at pH 5.5 monitored by dynamic light scattering (DLS)

The well-defined size distributions in FIG. 14 or the prolonged stability of generated vesicle diameter seem in FIG. 11 and FIG. 12 are indicators for a damped net surface charge after fusion. As a consequence consecutive fusions are hampered and the system displays a spontaneous feedback loop.

Example 8

Hybridosome Mediated Gene Transfer Leads to GFP Expression

Figure 15:
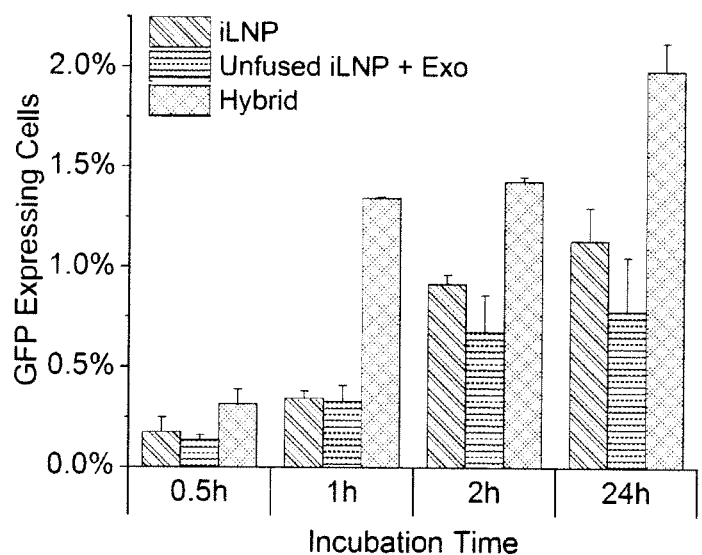
FIG. 15 is a graph showing the flow cytometry analysis of GFP expressing cells 72 h post transfection of equivalent amounts of pDNA in iLNPs, unfused iLNPs with exosomes, and hybridosomes. The time indicates transfection times.

To demonstrate functionality of hybridosome mediated delivery of genetic cargo, hybridosomes were manufactured from GBM cell line exosomes and iLNPs encapsulating a GFP plasmid. The expression of reporter GFP in GBM cells transfected with test formulations was analyzed by flow cytometry and confocal microscopy. Cells (50'000 cells seeded the prior day) were transfected with iLNPs (500 ng GFP-pDNA per well) and loaded hybridosomes (5 μg total protein/500 ng GFP-pDNA per well). Hybridosomes were manufactured prior to transfection by mixing exosomes with pDNA-iLNPs in fusion buffer for 30 min. In order to rule out that transfection is a result of fortuitous internalization of iLNPs due to exosome-induced endocytosis, cells were also co-transfected with unfused iLNPs (500 ng GFP-pDNA per well) and exosomes (5 μg total protein per well). After transfection times of 0.5 h, 1 h, 2 h or 24 h, cells were washed twice with PBS, fresh medium was added and cells were cultured for 72 h. The amount of GFP-expressing cells was analyzed flow cytometry (see FIG. 15). Hybridosomes show higher transfection rates compared to pDNA-iLNPs or unfused pDNA-iLNPs that were co-transfected with exosome.

Example 9

Purification of Hybridosomes

To exclude interference of unfused iLNPs in transfection experiments, they were separated from hybridosomes by continuous sucrose density gradient centrifugation. To determine the density of pDNA-iLNPs, they were centrifuged on 0-55% continuous sucrose (wt/vol) gradients (190'000 g, 14 h) and the column was fractionated. The density of sucrose fractions was determined by a refractometer and presence of particles was analyzed by photon count in DLS. The data reveals a 1.05 g/ml maximum density of pDNA-iLNPs (see FIG. 16).

Centrifugation of a pDNA-iLNP/exosome fusion mixtures (protein-to-plasmid ratio of 1:0.1, wt:wt) on a corresponding sucrose gradient yielded a distinctly opalescent band containing the unfused iLNPs at the top of the gradient. Sucrose fractions that corresponded to particles with densities 1.06-1.08, 1.09-1.18, and 1.19-1.25 g/ml were pooled and the sucrose was removed by dialysis against PBS.

Figure 16:
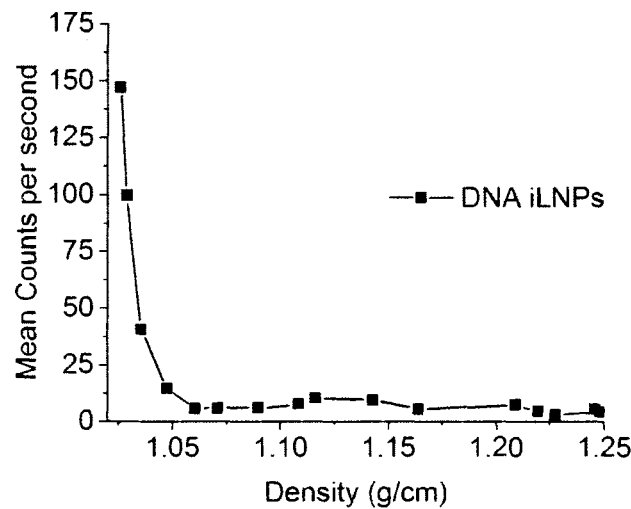
FIG. 16 is a graph showing the DLS mean photons per second indicative of the presence of nanoparticles in each density fraction of sucrose gradient of pDNA-iLNPs.
Figure 17:
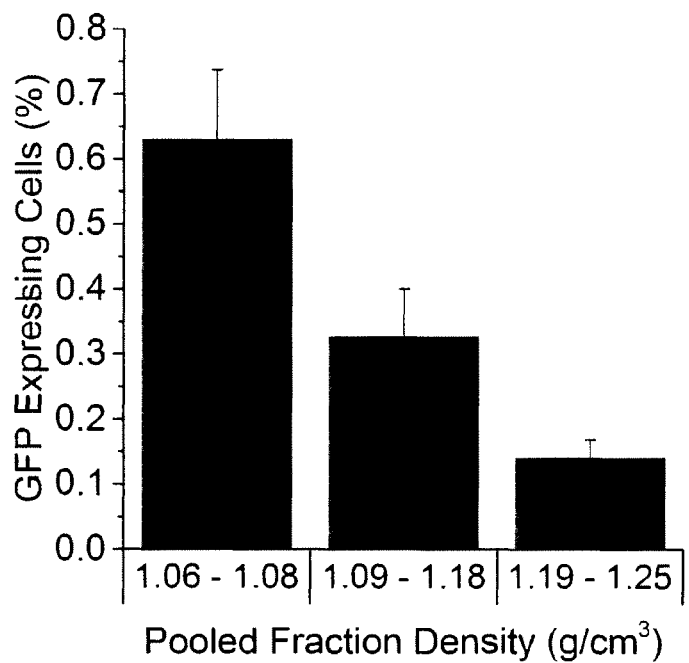
FIG. 17 is a graph showing the results of a flow cytometry analysis of GFP expressing cells 72 h post transfection with pooled particle density.

The ability of these fractions to transfect GFP was monitored by incubating with cells (72 h, 50'000 cells/well) and analyzing the number of GFP expressing cells by flow cytometry. As shown in FIG. 17 FIG. 16, all fractions resulted in GFP expression.

Figure 18:
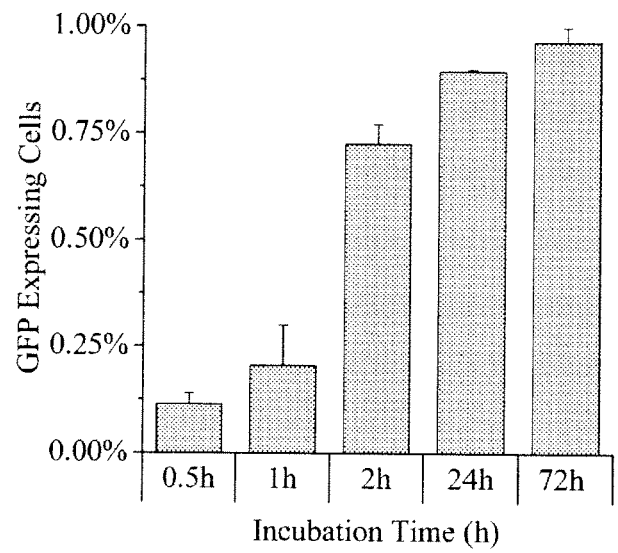
FIG. 18 is a graph showing the results of a flow cytometry analysis of GFP expressing cells 72 h post transfection of equivalent amounts of purified hybridosomes. The time indicates transfection times.

The pDNA-hybridosomes (particles below 1.05 g/ml) were pooled, the sucrose was removed by dialysis and they were retested in independent transfection studies. Cells (50'000 cells) were transfected with pDNA-hybridosomes ((2.5 μg protein/well based on BCA assay of the pooled fraction) for 0.5 h, 1 h, 2 h or 24 h. After the indicated transfection times, cells were washed twice with PBS and fresh culture medium was added. The amount of GFP-expressing cells after culturing for 72 h was analyzed by flow cytometry (see FIG. 18)

Example 10

Exogenous Targeting Moieties on Hybridosomes

The IgG surface modified iLNPs shown above were used to prepare hybridosomes with IgG fragments on the surface. Analogous to the enrichment of plasmid loaded hybridosomes in Example 9, IgG tethered iLNPs were mixed with GBM derived exosomes in fusion buffer for 30 minutes (6:1 weight ratio lipid to exosomal protein) and unfused iLNPs separated in a sucrose gradient. A particulate layer was visible at a density of 1.12-1.14 g/ml ($R_f=0.62$ compared to $R_f=0.36$ for plasmid loaded hybridosomes). Fractions below 1.08 g/ml were pooled and residual sucrose was removed via dialysis against PBS. Gel electrophoresis (SDS-PAGE) under non-reducing conditions using 10% acrylamide was conducted to verify the presence of both IgGs and exosomal protein.

Figure 19:
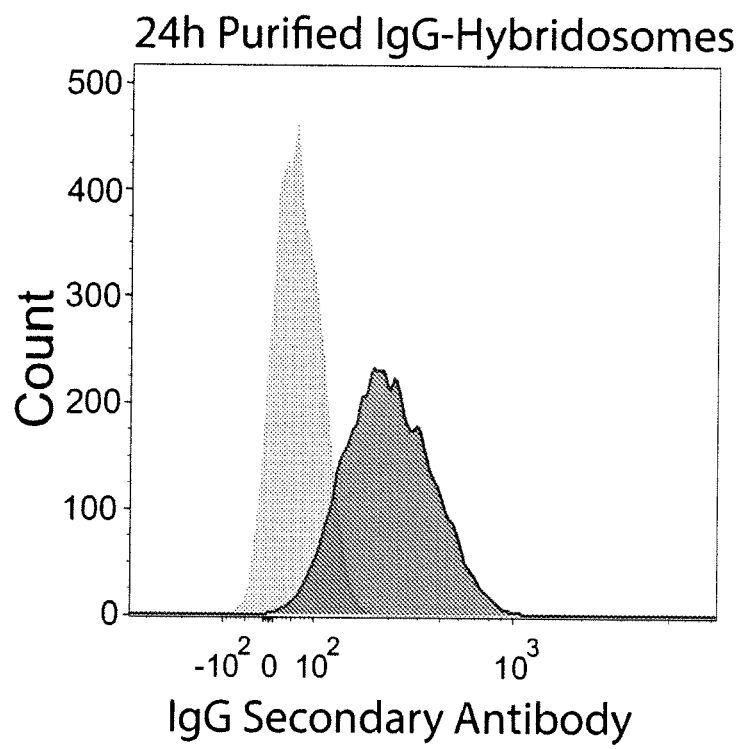
FIG. 19 is a graph showing the results of flow cytometry of 24 h incubation of purified IgG hybridosomes labeled with IgG secondary antibodies (control: light gray, IgG secondary antibody: gray)

The GBM cell line (50'000 cells per well seeded the prior day) was transfected with sucrose gradient purified IgG-hybridosomes (1.4 μg protein content per well as determined by BCA assay). Following 24 h of incubation, cells were washed and, as shown in FIG. 19, flow cytometry determined roughly 80% cells positive for the secondary anti-IgG labeled antibody.

Example 11

Diverse EDEMs for Versatile Hybridosomes

The ability to produce distinct hybridosomes by varying EDEM cargo or surface modification was determined by two types of fusion assays.

Figure 20:
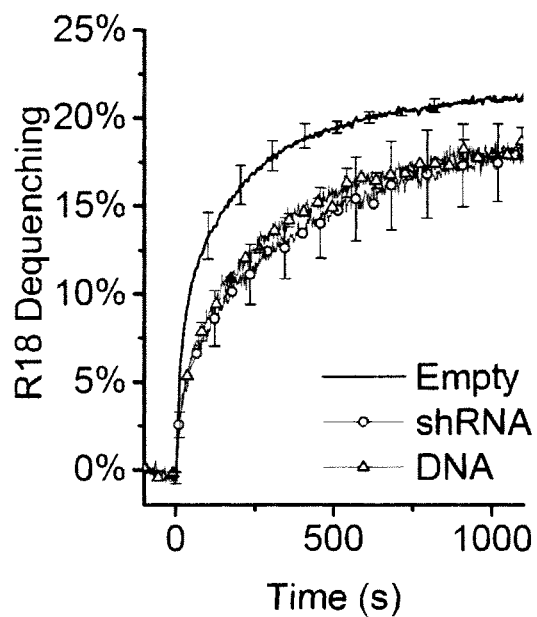
FIG. 20 is a graph showing the results of a R18 fusion assay of exosomes and iLNPs containing oligonucleotides.
Figure 21:
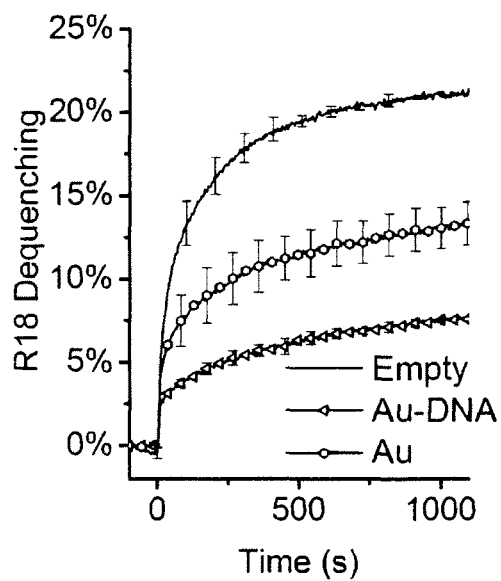
FIG. 21 is a graph showing the results of a R18 fusion assay of exosomes and solid nanoparticles encapsulating iLNPs or oligonucleotide/nanoparticles co-encapsulating iLNPs.
Figure 22:
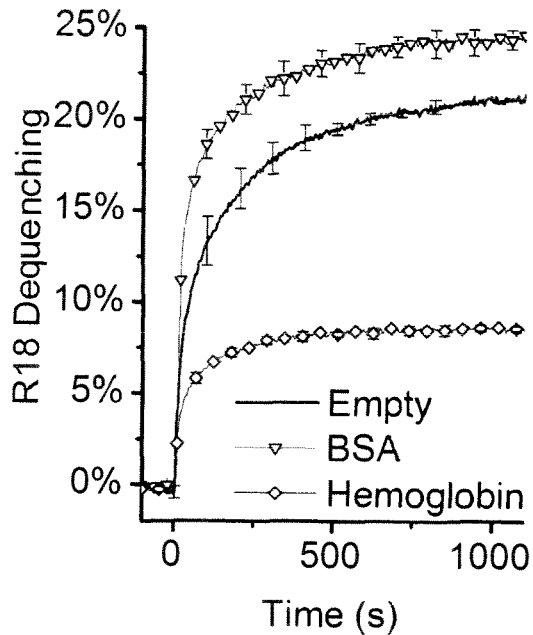
FIG. 22 is a graph showing the results of a R18 fusion assay of exosomes and protein encapsulating iLNPs.
Figure 23:
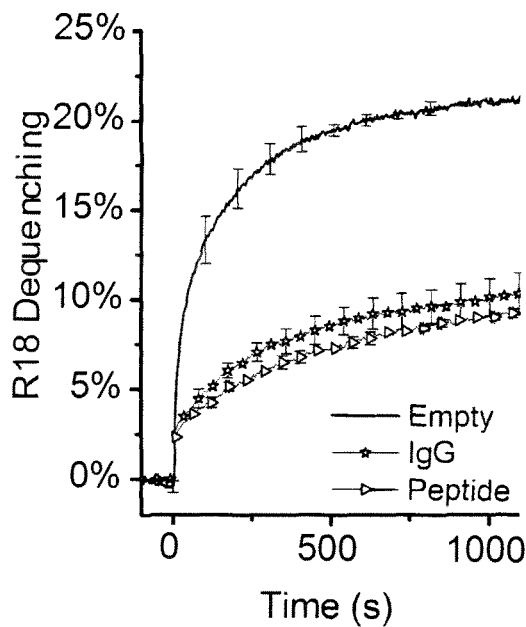
FIG. 23 is a graph showing the results of a R18 fusion assay of exosomes and surface modified iLNPs.

A R18 assay was performed as outlined in example 5. In short, fusion was determined by mixing the different iLNPs species shown in Example 1 with R18 labeled GBM cell line derived exosomes in fusion buffer. Fusion with iLNPs encapsulating oligonucleotides, protein and gold nanoparticles (gold nanoparticles alone or co-encapsulated with pDNA) are shown in FIG. 20 through FIG. 22. Fusion between exosomes and iLNPs with peptide and IgG surface modification is shown in FIG. 23.

A pyrene assay was employed to determine the fusion of MCL-exosomes with siRNA loaded iLNPs. These siRNA-iLNPs were manufactured by extrusion or by rapid mixing microfluidic chip (as outlined in Example 1).

Figure 24:
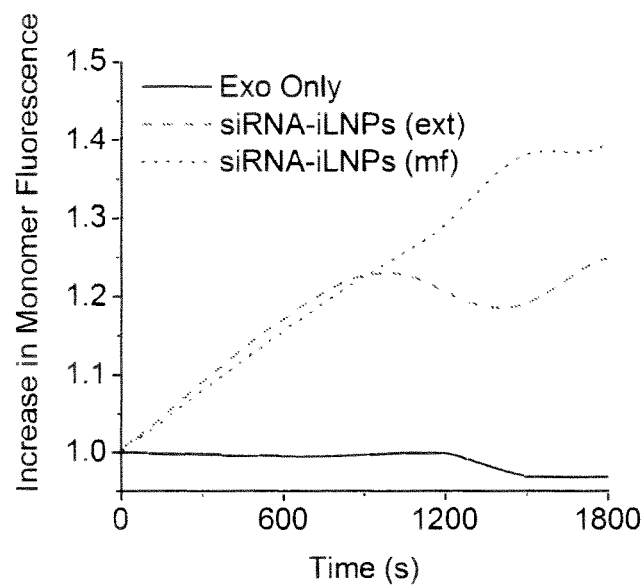
FIG. 24 is a graph showing the results of a pyrene fusion assay of MCL-exosomes alone or mixed with iLNPs manufactured by microfluidic fast mixing or by extrusion.

This assay is based on the increase of monomer fluorescence (approx. 400 nm) due to the dilution of pyrene excimers upon fusion of labeled membranes with unlabeled membranes. Exosomes (35 µg of total protein) in 100 µl of PBS were labelled with 1 µl of an 2.5 mM ethanolic solution of 1-pyrenedodecanoic acid (Life Technologies) for 30 min at 37° C. The excess 1-pyrenedodecanoic acid was removed by two-fold pelleting and washing with MES buffer (0.2M MES, 150 mM NaCl, pH 5.5) via ultracentrifugation at 100,000 g for 60 min. After removal of the free pyrene, labeled exosomes (10 µg total protein/well) were suspended in MES buffer (0.2M MES 150 mM NaCl, pH 5.5) in a 96-well-plate. Increase in monomer fluorescence upon addition of unlabeled iLNPs (5 µg of total lipids) was recorded at 37° C. with a Synergy HT Microplate Reader (Biotek). As shown in FIG. 24 a rise in monomer signal occurs once exosomes are mixed with iLNPs produced by extrusion (ext) and microfluidic chip (mf).

Example 12

Extracellular Vesicles as a Biocompatible Delivery Modules for Versatile Hybridosomes Fusion between microvesicles secreted by various types of cells, and different iLNPs was determined by a R18 fusion assay.

As shown in example 2, human microvesicles were isolated from platelets (PLT-MVs) and polymorphonuclear neutrophils (PMN-MVs).

Analogous to Example 5, microvesicle samples (0.25 µg PLT-MVs and 1.2 µg PMN-MV total protein) were labeled with ethanolic solution of R18, followed by free dye removal. Increase in fluorescence was monitored upon addition of different iLNP species.

Figure 25:
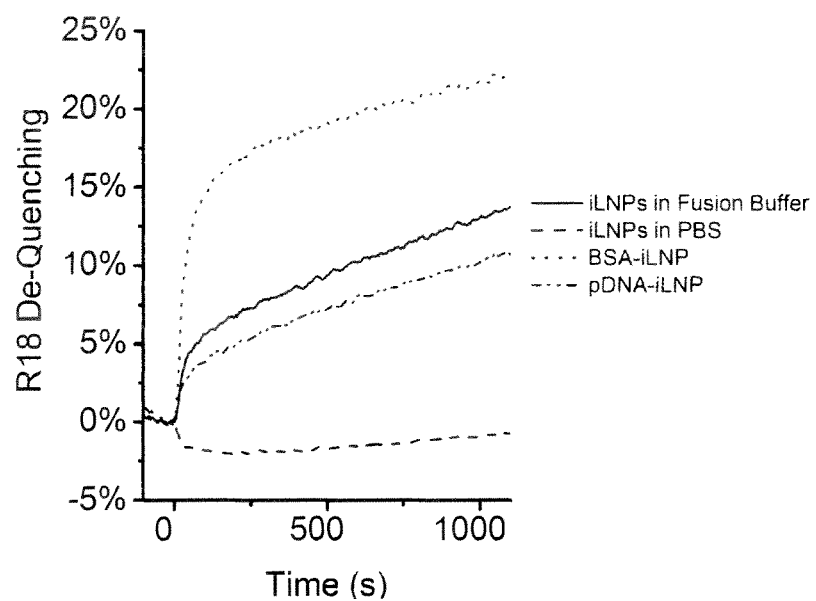
FIG. 25 is a graph showing the results of a R18 fusion assay of empty iLNPs and labeled PMN-MVs in fusion buffer or pH 7.4 buffer as well as iLNPs encapsulating different species of cargo.

As shown in FIG. 25, mixing iLNPs with PMN-MVs in fusion buffer resulted in de-quenching of R18. A pH dependent iLNP with PMN-MV interaction was determined as the addition of iLNPs at pH 7.4 resulted in no de-quenching. Mixing with pDNA-iLNPs and BSA-iLNPs resulted in R18-dequenching.

Figure 26:
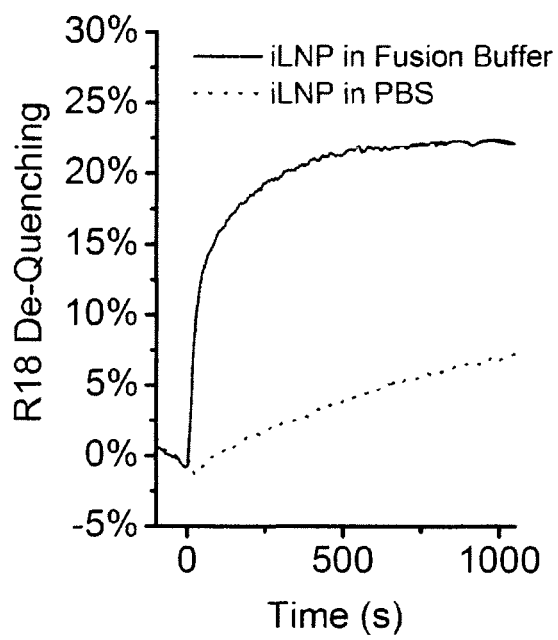
FIG. 26 is a graph showing the results of a R18 fusion assay of empty iLNPs and labeled PLT-MVs in fusion buffer or pH 7.0 buffer.

As shown in FIG. 26, mixing of PLT-MVs and empty iLNPs is pH dependent and similar to that of empty iLNPs and exosomes. PMN- and PLT-MVs are of particular interest as BDMs due to their anti-inflammatory and immunosuppressive properties. It has been shown that PMN-MVs can inhibit of cytokine release (tumor necrosis factor-α, transforming growth factor β1, interleukin-8, interleukin-10 and interleukin-12p70) and reduce immune activation receptors (CD40, CD80, CD83, CD86, CCR7, HLA-DP, HA-DQ and HA-DR) in human monocyte derived dendritic cells (Sadallah, Eken, & Schifferli, 2011).

Example 13

Cellular Uptake of Hybridosomes in Hard-to-Transfect Cells

Fluorescent microscopy was used to determine cellular uptake of hybridosomes by hard-to-transfect lymphocyte cell line (Jeko1). Hybridosomes were prepared from MCL-exo and NBD labeled iLNPs (iLNP formulation DlinDMA:Chol:DSPC:PEG-S-DMG:NBD-PC 40:40:17.5:2:0.5 formulation). MCL-Exo (2 µg total protein per well) were mixed with NBD labeled iLNPs (1 µg total lipids per well) in a reaction buffer (10 mM MES, pH 6.0, 145 mM NaCl, 5 mM KCl) and incubated on a shaker for 30 min at 37° C.

Figure 27:
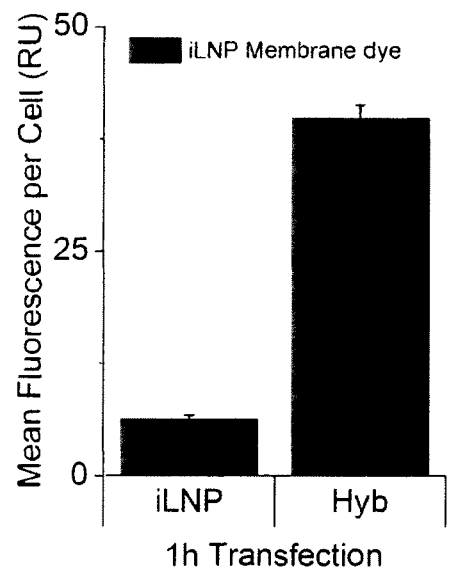
FIG. 27 is a histogram showing the mean fluorescence intensity of Jeko1 cells transfected for 1 h with hybridosomes made with NBD-labeled iLNPs or NBD-labeled iLNPs alone (n=160 cells, error bar indicates standard error).

Hybridosomes and iLNPs were transfected with target cells for 1 h and then twice washed with PBS to remove surface-bound and uninternalized vesicles. Cells were then resuspended in PBS and fluorescent images were made under identical instrument settings. Mean fluorescence intensity of iLNP membrane dye per cell was determined by image analysis in the open source software ImageJ. As shown in FIG. 27, Jeko1 cells (n=160) exhibited a nearly 7-times higher mean intensity of the iLNP membrane dye after 1 h transfection with hybridosomes than with iLNPs alone.

BIBLIOGRAPHY

Bao, G., Mitragotri, S., & Tong, S. (2013). Multifunctional nanoparticles for drug delivery and molecular imaging. *Annual Review of Biomedical Engineering*, 15, 253-82. doi:10.1146/annurev-bioeng-071812-15240

Belliveau, N. M., Huft, J., Lin, P. J., Chen, S., Leung, A. K., Leaver, T. J., . . . Cullis, P. R. (2012). Microfluidic Synthesis of Highly Potent Limit-size Lipid Nanoparticles for In Vivo Delivery of siRNA. *Molecular Therapy: Nucleic Acids*, 1(May), e37. doi:10.1038/mtna.2012.28

Eken, C., Sadallah, S., Martin, P. J., Treves, S., & Schifferli, J. a. (2013). Ectosomes of polymorphonuclear neutrophils activate multiple signaling pathways in macrophages. *Immunobiology*, 218(3), 382-92. doi:10.1016/j.imbio.2012.05.021

E L Andaloussi, S., Mäger, I., Breakefield, X. O., & Wood, M. J. a. (2013). Extracellular vesicles: biology and emerging therapeutic opportunities. *Nature Reviews Drug Discovery*, 12(5), 347-57. doi:10.1038/nrd3978

Haiss, W., Thanh, N. T. K., Aveyard, J., & Fernig, D. G. (2007). Determination of size and concentration of gold nanoparticles from UV-vis spectra. *Analytical Chemistry*, 79(11), 4215-21. doi:10.1021/ac0702084

Heyes, J., Palmer, L., Bremner, K., & MacLachlan, I. (2005). Cationic lipid saturation influences intracellular delivery of encapsulated nucleic acids. *Journal of Controlled Release*, 107(2), 276-87. doi:10.1016/j.jconrel.2005.06.014

Marcus, M. E., & Leonard, J. N. (2013). FedExosomes: Engineering Therapeutic Biological Nanoparticles that Truly Deliver. *Pharmaceuticals*, 6(5), 659-680. doi:10.3390/ph6050659

Maurer, N., Wong, K. F., Stark, H., Louie, L., McIntosh, D., Wong, T., . . . Cullis, P. R. (2001). Spontaneous entrapment of polynucleotides upon electrostatic interaction with ethanol-destabilized cationic liposomes. *Biophysical Journal*, 80(5), 2310-26. doi:10.1016/S0006-3495(01)76202-9

Sadallah, S., Eken, C., Martin, P. J., & Schifferli, J. a. (2011). Microparticles (ectosomes) shed by stored human platelets downregulate macrophages and modify the development of dendritic cells. *Journal of Immunology*, 186(11), 6543-52. doi:10.4049/jimmunol.1002788

Sadallah, S., Eken, C., & Schifferli, J. a. (2011). Ectosomes as immunomodulators. *Seminars in Immunopathology*, 33(5), 487-95. doi:10.1007/s00281-010-0232-x Semple, S. C., Akinc, A., Chen, J., Sandhu, A. P., Mui, B. L., Cho, C. K., . . . Hope, M. J. (2010). Rational design of cationic lipids for siRNA delivery. *Nature Biotechnology*, 28(2), 172-6. doi:10.1038/nbt.1602

Théry, C., Amigorena, S., Raposo, G., & Clayton, A. (2006). Isolation and characterization of exosomes from cell culture supernatants and biological fluids. *Current Protocols in Cell Biology*, Chapter 3, Unit 3.22. doi:10.1002/0471143030.cb0322s30

Vlassov, A. V, Magdaleno, S., Setterquist, R., & Conrad, R. (2012). Exosomes: current knowledge of their composition, biological functions, and diagnostic and therapeutic potentials. *Biochimica et Biophysica Acta*, 1820(7), 940-8. doi:10.1016/j.bbagen.2012.03.017

The invention claimed is:

1. A process for manufacturing a hybrid biocompatible carrier (hybridosome), said process comprising contacting a first vesicle with a second vesicle, thereby uniting said first vesicle with said second vesicle and producing said hybridosome,
    wherein said first vesicle has been produced in vitro, and said first vesicle comprises a fusogenic, ionizable cationic lipid, and wherein said first vesicle encapsulates a bioactive agent;
    wherein said second vesicle comprises a lipid bilayer, and wherein said second vesicle has been produced in vivo and is released into the extracellular environment; and
    wherein the contacting step is performed at a pH at which the fusogenic, ionizable cationic lipid is predominantly in a charged, cationic form.

2. The process of claim 1, wherein the contacting is performed in at least one of:
    a. in a buffer having a pH between 4 and 6; and
    b. at a reaction temperature of about 37° C.

3. The process of claim 1, wherein said first vesicle comprises an ionizable cationic lipid at a molar concentration of at least 30% of total lipid of the first vesicle.

4. The process of claim 1, wherein the bioactive agent is a therapeutic agent.

5. The process of claim 1, wherein the bioactive agent is:
    a. a drug or a pharmaceutically acceptable salt or derivative thereof;
    b. an antibody-based therapeutic agent; or
    c. a peptide, a protein, or a nucleic acid.

6. The process of claim 1, wherein:
    a. said first vesicle is selected from the group consisting of lipid-based nanoparticles (LNPs), liposomes, polymer-stabilized LNPs, cerasomes, sphingosomes, polymersomes, synthetic-nanoparticle stabilized LNPs, natural membrane-derived LNPs, and natural membrane-coated LNPs, and
    b. said second vesicle is selected from the group consisting of exosomes, ectosomes, microvesicles and apoptotic bodies.

7. The process of claim 1, wherein said ionizable cationic lipid is selected from the group consisting of 1,2-Dilinoleyloxy-N,N-dimethylaminopropane (DLinDMA), 2,2-dilinoleyl-4-(2-dimethylaminoethyl)-[1,3]-dioxolane (DLin-KC2-DMA), heptatriaconta-6,9,28,31-tetraen-19-yl4-(dimethylamino)butanoate (DLin-MC3-DMA), 1,2-dioleoyl-3-dimethylammonium-propane (DODAP), N-(4-carboxybenzyl)-N,N-dimethyl-2,3-bis(oleoyloxy)propan-1-aminium (DOBAQ), YSKO5, 4-(((2,3-bis(oleoyloxy)propyl)-(methyl)amino)methyl)benzoic acid (DOBAT), N-(4-carboxybenzyl)-N,N-dimethyl-2,3-bis(oleoyloxy)propan-1-aminium (DOBAQ), 3-((2,3-bis(oleoyloxy)propyl)(methyl)amino)propanoic acid (DOPAT), N-(2-carboxypropyl)-N,N-dimethyl-2,3-bis-(oleoyloxy)-propan-1-aminium (DOMPAQ), N-(carboxymethyl)-N,N-dimethyl-2,3-bis(oleoyloxy)propan-1-aminium (DOAAQ), Alny-100, 3-(dimethylamino)-propyl(12Z, 15Z)-3-[(9Z,12Z)-octadeca-9,12-dien-1-yl]-henicosa-12,15-dienoate (DMAP-BLP), and derivatives of ionizable amino-lipids.

8. The process of claim 1, wherein the process further comprises terminating said uniting process by increasing the pH of the environment of said contacting step.

9. A hybridosome, wherein said hybridosome is manufactured by a process comprising contacting a first vesicle with a second vesicle, thereby uniting said first vesicle with said second vesicle and producing said hybridosome,
    wherein said first vesicle has been produced in vitro, and said first vesicle comprises a fusogenic, ionizable cationic lipid at a molar concentration of at least 30% of total lipid of the first vesicle,
    wherein said first vesicle encapsulates a bioactive agent; and
    wherein said second vesicle comprises a lipid bilayer, and wherein said second vesicle has been produced in vivo and is released into the extracellular environment.

10. The hybridosome of claim 9, wherein the contacting is performed in at least one of:
    a. in a buffer having a pH between 4 and 6; and
    b. at a reaction temperature of about 37° C.

11. The hybridosome of claim 9, wherein the bioactive agent is a therapeutic agent.

12. The hybridosome of claim 9, wherein the bioactive agent is:
    a. a drug or a pharmaceutically acceptable salt or derivative thereof;
    b. an antibody-based therapeutic agent; or
    c. a peptide, a protein, or a nucleic acid.

13. The hybridosome of claim 9, wherein:
    a. said first vesicle is selected from the group consisting of lipid-based nanoparticles (LNPs), liposomes, polymer-stabilized LNPs, cerasomes, sphingosomes, polymersomes, synthetic-nanoparticle stabilized LNPs, natural membrane-derived LNPs, and natural membrane-coated LNPs, and
    b. said second vesicle is selected from the group consisting of exosomes, ectosomes, microvesicles and apoptotic bodies.

14. The hybridosome of claim 9, wherein said ionizable cationic lipid is selected from the group consisting of 1,2-Dilinoleyloxy-N,N-dimethylaminopropane (DLin-DMA), 2,2-dilinoleyl-4-(2-dimethylaminoethyl)-[1,3]-dioxolane (DLin-KC2-DMA), heptatriaconta-6,9,28,31-tetraen-19-yl4-(dimethylamino)butanoate (DLin-MC3-DMA), 1,2-dioleoyl-3-dimethylammonium-propane (DODAP), N-(4-carboxybenzyl)-N,N-dimethyl-2,3-bis(oleoyloxy)propan-1-aminium (DOBAQ), YSKO5, 4-(((2,3-bis(oleoyloxy)propyl)-(methyl)amino)methyl)benzoic acid (DOBAT), N-(4-carboxybenzyl)-N,N-dimethyl-2,3-bis(oleoyloxy)propan-1-aminium (DOBAQ), 3-((2,3-bis(oleoyloxy)propyl)(methyl)amino)propanoic acid (DOPAT), N-(2-carboxypropyl)-N,N-dimethyl-2,3-bis-(oleoyloxy)-propan-1-aminium (DOMPAQ), N-(carboxymethyl)-N,N-dimethyl-2,3-bis(oleoyloxy)propan-1-aminium (DOAAQ), Alny-100, 3-(dimethylamino)-propyl(12Z, 15Z)-3-[(9Z,12Z)-octadeca-9,12-dien-1-yl]-henicosa-12,15-dienoate (DMAP-BLP), and derivatives of ionizable amino-lipids.

15. A pharmaceutical composition comprising the hybridosome of claim 9.

16. A method for delivering a bioactive agent into a cell, wherein said method comprises contacting a hybridosome comprising the bioactive agent with the cell, and wherein said hybridosome is manufactured by a process comprising contacting a first vesicle with a second vesicle, thereby uniting said first vesicle with said second vesicle and producing said hybridosome,
- wherein said first vesicle has been produced in vitro, and said first vesicle comprises a fusogenic, ionizable cationic lipid at a molar concentration of at least 30% of total lipid of the first vesicle,
- wherein said first vesicle encapsulates the bioactive agent; and
- wherein said second vesicle comprises a lipid bilayer, and wherein said second vesicle has been produced in vivo and is released into the extracellular environment.

17. The method of claim 16, wherein the contacting of said first and second vesicles is performed in at least one of:
   a. in a buffer having a pH between 4 and 6; and
   b. at a reaction temperature of about 37° C.

18. The method of claim 16, wherein the bioactive agent is a therapeutic agent.

19. The method of claim 16, wherein the bioactive agent is
   a. a drug or a pharmaceutically acceptable salt or derivative thereof;
   b. an antibody-based therapeutic agent; or
   c. a peptide, a protein, or a nucleic acid.

20. The method of claim 16, wherein the cell is a leukocyte, a glial cell or a cell during an ex vivo expansion.

21. The method of claim 16, wherein:
   a. said first vesicle is selected from the group consisting of lipid-based nanoparticles (LNPs), liposomes, polymer-stabilized LNPs, cerasomes, sphingosomes, polymersomes, synthetic-nanoparticle stabilized LNPs, natural membrane-derived LNPs, and natural membrane-coated LNPs, and
   b. said second vesicle is selected from the group consisting of exosomes, ectosomes, microvesicles and apoptotic bodies.

22. The method of claim 16, wherein said ionizable cationic lipid is selected from the group consisting of 1,2-Dilinoleyloxy-N,N-dimethylaminopropane (DLinDMA), 2,2-dilinoleyl-4-(2-dimethylaminoethyl)-[1,3]-dioxolane (DLin-KC2-DMA), heptatriaconta-6,9,28,31-tetraen-19-yl4-(dimethylamino)butanoate (DLin-MC3-DMA), 1,2-dioleoyl-3-dimethylammonium-propane (DO-DAP), N-(4-carboxybenzyl)-N,N-dimethyl-2,3-bis(oleoyloxy)propan-1-aminium (DOBAQ), YSKO5, 4-(((2,3-bis(oleoyloxy)propyl)-(methyl)amino)methyl)benzoic acid (DOBAT), N-(4-carboxybenzyl)-N,N-dimethyl-2,3-bis(oleoyloxy)propan-1-aminium (DOBAQ), 3-((2,3-bis(oleoyloxy)propyl)(methyl)amino)propanoic acid (DOPAT), N-(2-carboxypropyl)-N,N-dimethyl-2,3-bis-(oleoyloxy)-propan-1-aminium (DOMPAQ), N-(carboxymethyl)-N,N-dimethyl-2,3-bis(oleoyloxy)propan-1-aminium (DOAAQ), Alny-100, 3-(dimethylamino)-propyl(12Z, 15Z)-3-[(9Z, 12Z)-octadeca-9,12-dien-1-yl]-henicosa-12,15-dienoate (DMAP-BLP), and derivatives of ionizable amino-lipids.

23. The method of claim 16, wherein said first vesicle further comprises a targeting moiety, wherein the targeting moiety is selected from the group consisting of antibodies or fragments thereof, antibody-like molecules, peptides, proteins, aptamers, oligonucleotides and polysaccharides.

24. The method of claim 16, wherein said first vesicle further comprises a PEG-modified lipid selected from the group consisting of a PEG-phospholipid, PEG-modified phosphatidylethanolamine (PEG-PE), PEG-modified ceramides, PEG-modified dialkylamines, PEG-modified diacylglycerols, polyethylene glycol dipalmitoylglycerol (PEG-DPG), PEG-modified dialkylglycerols, (methoxy polyethylene glycol)-dimyristolglycerol (PEG-s-DMG), a PEG-dialkyloxypropyl (DAA),R-3-[(w-methoxy-poly(ethyleneglycol)2000)carbamoyl)]-1,2-dimyristyloxypropyl-3-amine (PEG-c-DOMG), and N-acetylgalactosamine-((R)-2,3-bis(octadecyloxy)propyl-1-(methoxy-poly(ethylene glycol)2000)propylcarbamate)) (GalNAc-PEG-DSG).

25. The method of claim 16, wherein said second vesicle is derived from:
   a. a tumor cell of a cancer or pre-cancer patient, or is derived from a tumor or cancer cell line;
   b. a glioblastoma cells or a mantle cell lymphoma cell;
   c. a cell selected from the group consisting of B-cells, antigen presenting cells, lymphocytes, thrombocytes, neutrophils, activated polymorphonuclear neutrophils and leukocytes;
   d. a bacterial pathogen, amoebic pathogen, parasitic pathogen or fungal pathogen; or
   e. a pathogen infected cell.

26. The method of claim 16, wherein said first vesicle further comprises a nucleic acid selected from the group consisting of small interfering RNA (siRNA), antisense RNA, micro RNA (miRNA), small or short hairpin RNA (shRNA), guide RNA (gRNA), clustered regularly interspaced short palindromic repeat RNA (crRNA), trans-activating clustered regularly interspaced short palindromic repeat RNA (tracrRNA), immune-stimulating oligonucleotides, plasmids, antisense nucleic acids and ribozymes.

27. The method of claim 16 wherein:
   a. said first vesicle comprises at least one of a modified nucleic acid molecule and mRNA which encodes at least one antigen; or
   b. said second vesicle comprises a disease-associated antigen selected from the group consisting of a tumor-associated antigen and a pathogen-associated antigen.

28. The method of claim 16, wherein said first vesicle comprises an agent selected from the group consisting of:
   a. a radioisotope selected from 225Ac, 72As, 211At, 11B, 128Ba, 212Bi, 75Br, 77Br, 14C, 109Cd, 62Cu, 64Cu, 67Cu, 18F, 67Ga, 68Ga, 3H, 123I, 125I, 130I, 131I, 111In, 177Lu, 13N, 15O, 32P, 33P, 212Pb, 186Re, 188Re, 47Sc, 153Sm, 89Sr, 99mTc, 88Y, and 90Y; and
   b. a quantum dot, and a metal nanoparticle selected from a gold, a silver, an iron oxide and an iron nanoparticle.

29. A hybridosome comprising
a therapeutic agent encapsulated by a membrane of the hybridosome; wherein the membrane of the hybridosome comprises:
   a. elements of a membrane of a first vesicle, wherein the elements of a membrane of the first vesicle comprise a fusogenic, ionizable cationic lipid, wherein said fusogenic, ionizable cationic lipid has at least one protonatable or deprotonatable group, such that the lipid is positively charged at a pH below physiological pH and neutral above physiological pH, and wherein said first vesicle has been produced in vitro such that the fusogenic, ionizable cationic lipid is present at a molar concentration of at least 30% of total lipid of the first vesicle; and
   b. elements of a lipid bilayer of a second vesicle, wherein said second vesicle has been produced in vivo and is released into the extracellular environment.

30. The hybridosome of claim 29, wherein
   a. the first vesicle is an exosome, ectosome, microvesicle, or apoptotic body; and
   b. the second vesicle is a lipid-based nanoparticle (LNP), liposome, polymer-stabilized LNP, cerasome, sphingosome, polymersome, synthetic-nanoparticle stabilized LNP, natural membrane-derived LNP, or natural membrane-coated LNP.

31. The hybridosome of claim 29, wherein
   a. the first vesicle is an exosome; or
   b. the second vesicle is an LNP.

32. The hybridosome of claim 29, wherein
   a. the first vesicle is an exosome; and
   b. the second vesicle is an LNP.

33. The hybridosome of claim 29 wherein the hybridosome comprises a lipid of an exosome, ectosome, microvesicle, or apoptotic body.

34. The hybridosome of claim 33, wherein the exosome, ectosome, microvesicle, or apoptotic body is a naturally secreted exosome, ectosome, microvesicle or apoptotic body.

35. The hybridosome of claim 29 wherein the hybridosome further comprises a targeting moiety selected from the group consisting of antibodies or fragments thereof, antibody-like molecules, peptides, proteins, aptamers, oligonucleotides, sugars, polysaccharides and vitamins.

36. The hybridosome of claim 35, wherein said targeting moiety binds to a moiety on the cell surface of a target cell.

37. The hybridosome of claim 29 wherein the hybridosome further comprises a fusion peptide anchored to its surface, wherein said fusion peptide is selected from soluble N-ethyl maleimide sensitive factor attachment protein receptors (SNARE proteins) and synthetics mimics thereof.

38. The hybridosome of claim 29 wherein the hybridosome further comprises a PEG-modified lipid.

39. The hybridosome of claim 29, wherein the therapeutic agent is:
   a. a drug or a pharmaceutically acceptable salt or derivative thereof;
   b. an antibody-based therapeutic agent; or
   c. a peptide, a protein, or a nucleic acid.

* * * * *